United States Patent [19]

Iida et al.

[11] Patent Number: 5,583,208
[45] Date of Patent: Dec. 10, 1996

[54] GANGLIOSIDE GM3 DERIVATIVES CONTAINING FLUORINE IN CERAMIDE PORTION

[75] Inventors: Takao Iida; Yutaka Ohira, both of Tsukuba, Japan

[73] Assignee: Daikin Industries, Ltd., Osaka, Japan

[21] Appl. No.: 432,185

[22] PCT Filed: Sep. 9, 1994

[86] PCT No.: PCT/JP94/01495

§ 371 Date: May 8, 1995

§ 102(e) Date: May 8, 1995

[87] PCT Pub. No.: WO95/07302

PCT Pub. Date: Mar. 16, 1995

[30] Foreign Application Priority Data

Sep. 10, 1993 [JP] Japan .................................. 5-225764
Dec. 27, 1993 [JP] Japan .................................. 5-331661

[51] Int. Cl.$^6$ .................... C07H 15/02; C07H 1/00; A61K 31/70
[52] U.S. Cl. .................... 536/17.9; 536/17.2; 536/18.4; 536/18.5; 552/10; 568/495; 514/25
[58] Field of Search ................. 536/17.2, 17.9, 536/18.4, 18.5; 552/10; 568/495; 514/25

[56] References Cited

U.S. PATENT DOCUMENTS 4,851,511  7/1989  Hakomori et al. .............. 530/387.5
4,880,572  11/1989  Fujita et al. ..................... 554/66

FOREIGN PATENT DOCUMENTS 63-159402  7/1988  Japan .
03101691  4/1991  Japan .

OTHER PUBLICATIONS

S. Hakomori, J. Biol. Chem., vol. 265, No. 31, pp. 18713–18716 (1990).
M. Iwamori, Yukagaku, vol. 40, pp. 361–369 (1991).
A. Hasegawa et al., Carbohydr. Res., vol. 230, pp. 273–288 (1992).
A. Hasegawa et al., J. Carbohydr. Chem., vol. 9(2&3), pp. 201–214 (1990).
K. Fukase et al., Tetrahedron Letters, vol. 34, No. 13, pp. 2187–2190 (1993).

*Primary Examiner*—Gary L. Kunz
*Assistant Examiner*—Kathleen Kahler Fonda

[57] ABSTRACT

A ganglioside GM3 derivative containing fluorine atoms in a ceramide portion thereof, represented by the formula:

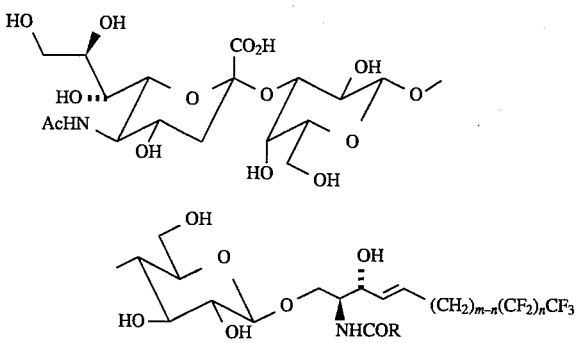

in which m is an integer of at least 2, n is an integer of 0 to 7 provided that m is larger than n, and R represents an alkyl group or a fluoroalkyl group is disclosed.

4 Claims, No Drawings

GANGLIOSIDE GM3 DERIVATIVES CONTAINING FLUORINE IN CERAMIDE PORTION

FIELD OF THE INVENTION

The present invention relates to a ganglioside GM3 derivative containing fluorine atoms in a ceramide portion thereof, to intermediates thereof and to processes for preparing the same.

DESCRIPTION OF THE PRIOR ART

Glycolipids of mammals belong to a sphingoglycolipid which consists of a lipid portion so called ceramide in which a sphingosine of a long chain aminoalcohol is bonded to a long chain carboxylic acid via an amide linkage, a oligosaccharide chain in various types and sialic acid. Ganglioside is a collective name of sphingoglycolipids which particularly contain sialic acid.

Many of the gangliosides are generally localized on cell surfaces of animals, and a sialic saccharide chain portion thereof is directed to outside of the cell. Recent studies reveal that the gangliosides play an important role in fundamental life phenomena such as discrimination in cells, reception and response of information in cells, receptor function for hormone, virus, bacteria, cell toxin, etc., interceller distinction, differentiation and propagation of cells, malignant alteration, immunity, etc.

Among the gangliosides, attention is paid to ganglioside GM3 as a molecule which can develop various physiological activities relating to information communication in cells, differentiation and propagation of cells (S. Hakomori, J. Biol. Chem., 265 (1990), 18713–18716; M. Iwamori, Yukagaku, 40, 361–369 (1991)). In order to clarify the relationship between molecular structures of GM3 derivatives and physiological activities thereof, it is important to prepare various types of the GM3 derivatives which are constituents of biomembrane. Hasegawa synthesized a GM3 derivative in which a sialic acid portion thereof was modified in order to make the role of the sialic acid portion in ganglioside GM3 clear (A. Hasegawa, Carbohydr. Res., 230, 273 (1992)). However, modification of a ceramide portion in the ganglioside GM3 has scarcely been effected (A. Hasegawa et al., Carbohydr. Res., 9, 201 (1990)). If a GM3 derivative in which the ceramide portion thereof is modified is synthesized, physiological significance of the ceramide portion is expected to be made clear.

Hasegawa et al. also found out a process for introducing sialic acid to a specific position in a saccharide chain, which process is important for systematic and easy synthesis of gangliosides, and filed for patent application (Japanese Patent Kokai No. 101691/1991). However, according to the process, dimethyl(methylthio)sulfonium triflate (referred to as DMTST hereinafter) which is a reaction accelerator must be prepared immediately before the reaction. In addition, it is extremely difficult to reproduce a yield of 47%, which is described in the patent literature, in the synthesis of a sialyllactose portion which is a saccharide chain of ganglioside GM3 (see Comparative Example 1 of the present invention).

Kusumoto et al. report synthesis of a sialyllactose portion using similar compounds by a combination of N-bromosuccinimide and tetrabutylammonium triflate as reaction accelerators (K. Fukase et al., Tetrahedron Lett., 34, 2187, (1993)). The present inventor attempted to follow the process. However, the intended sialylation did not proceed at all, and the lactose portion used as a starting substance was quantitatively recovered (see Comparative Example 2 of the present invention). Therefore, it is desired to provide a simpler process for synthesizing GM3 intermediates in higher yield.

SUMMARY OF THE INVENTION

It is an object of the present invention to provide a GM3 derivative having fluorine atoms in a ceramide portion thereof which is a lipid portion of ganglioside GM3, and intermediates thereof.

The present invention provides a fluorinated ganglioside GM3 derivative of the general formula (I):

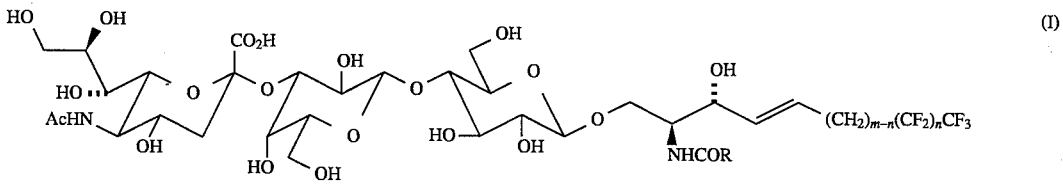

in which m is an integer of at least 2, n is an integer of 0 to 7 provided that m is larger than n, and R represents an alkyl group or a fluoroalkyl group.

The present invention also provides a fluorinated 2-azide sphingosine of the general formula (II):

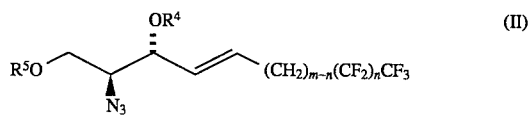

in which m is an integer of at least 2, n is an integer of 0 to 7 provided that m is larger than n, $R^4$ and $R^5$ independently represent a hydrogen atom or a protective group for a hydroxyl group, which is an intermediate of the compound represented by the general formula (I).

The present invention also provides a fluorinated α,β-unsaturated aldehyde of the general formula (III):

in which m is an integer of at least 2, n is an integer of 0 to 7 provided that m is larger than n,
which is an intermediate of the compound represented by the general formula (II).

Furthermore, the present invention provides a process for preparing a ganglioside GM3 intermediate of the general formula (VI):

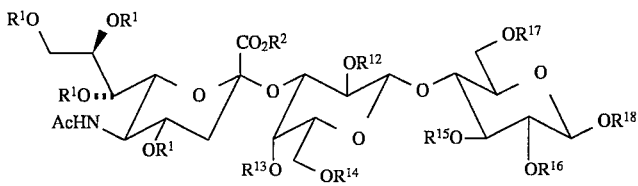

in which $R^1$ represents a protective group for a hydroxyl group, $R^2$ represents a protective group for a carboxylic acid, $R^{12}$, $R^{13}$, $R^{14}$, $R^{15}$, $R^{16}$, and $R^{17}$ independently represent a hydrogen atom or a protective group for a hydroxyl group, and $R^{18}$ represents a trialkylsilylethyl group in which the alkyl group contains 1 to 4 carbon atoms, which comprises the step of reacting a compound of the general formula (IV):

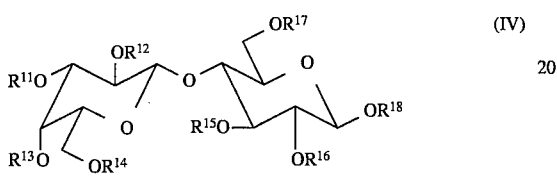

in which $R^{11}$ represents a hydrogen atom or a protective group for a hydroxyl group, and $R^{12}$ to $R^{18}$ are the same as defined above, with a compound of the general formula (V):

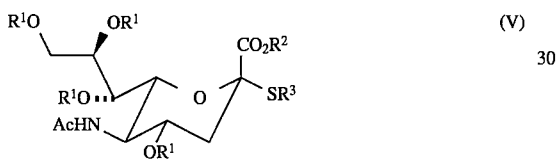

in which $R^1$ and $R^2$ are the same as defined above, and $R^3$ represents an alkyl group containing 1 to 10 carbon atoms or a phenyl group optionally having substituents, in the presence of N-iodosuccineimide and trifluoromethanesulfonate

DETAILED DESCRIPTION OF THE INVENTION

The ganglioside GM3 derivative of the general formula (I) according to the present invention containing fluorine atoms in a ceramide portion thereof is, for example, synthesized in the following sequence:

(1) Synthesis of a fluorinated α,β-unsaturated aldehyde
(2) Synthesis of a fluorinated 2-azide sphingosine from the fluorinated α,β-unsaturated aldehyde
(3) Condensation of a GM3 saccharide chain portion with the fluorinated 2-azide sphingosine
(4) Reduction of an azide group in the condensed product to an amino group
(5) Condensation of the aminated condensed product with a carboxylic acid
(6) Elimination of protective groups The reactions will be illustrated in order hereinafter.

(1) Synthesis of a fluorinated α,β-unsaturated aldehyde

At first, a fluorinated α,β-unsaturated aldehyde of the general formula (III) is synthesized for example in the following route:

(1-1) Scheme 1

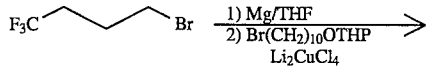

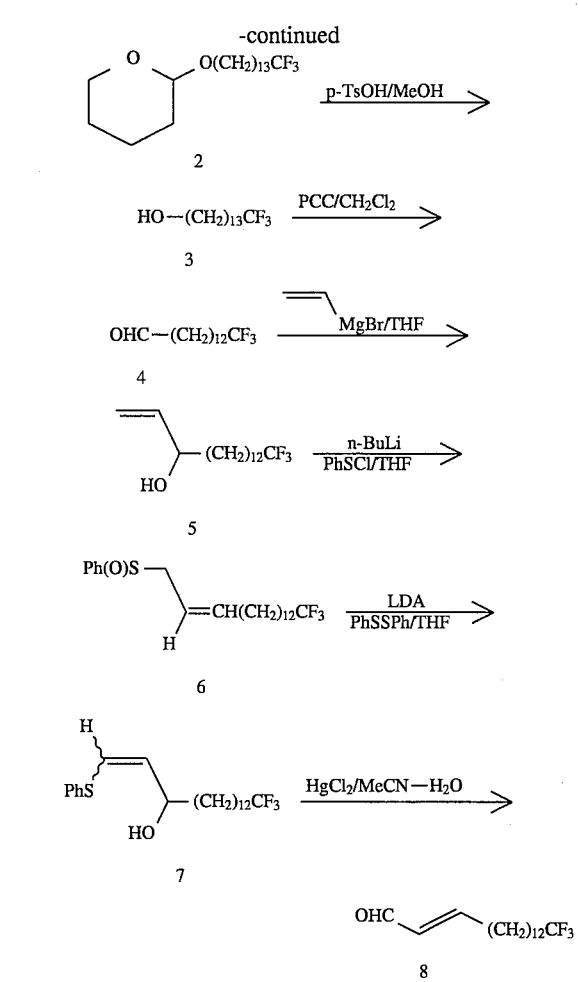

Notes:
$Br(CH_2)_{10}OTHP$: 10-bromo-1-[(3,4,5,6-tetrahydro-2H-pyran-2-yl) oxy]tetradecane
p-TsOH: p-toluenesulfonic acid
PCC: pyridinium clorocromate
PhSCl: benzenesulfenyl chloride
LDA: lithium diethylamide
PhSSPh: diphenyl sulfide Details of reaction conditions in every reaction are described in Examples 2 to 8.

(1-2) Scheme 2

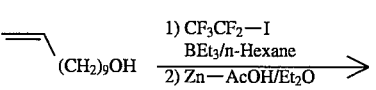

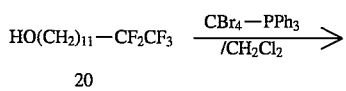

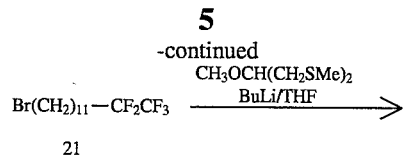
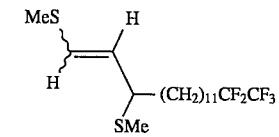
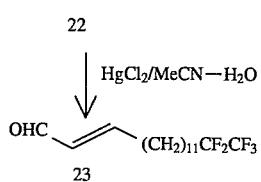

Details of reaction conditions in every reaction are described in Examples 20 to 23

(1-3) Scheme 3

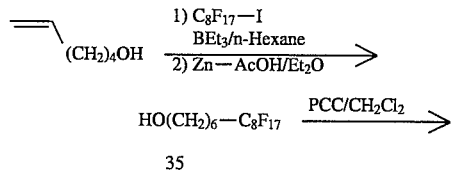
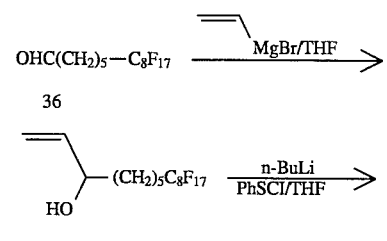
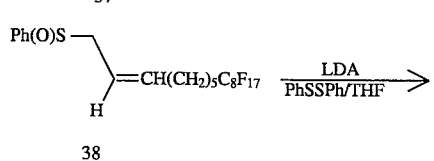
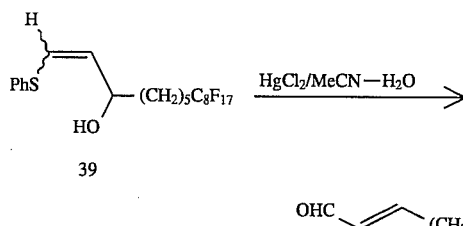
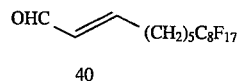

Details of reaction conditions in every reaction are described in Examples 35 to 40.

It can be understood that appropriate selection of starting substances provides the fluorinated α,β-unsaturated aldehyde of the general formula (III).

(2) Synthesis of a fluorinated 2-azide sphingosine

A fluorinated 2-azide sphingosine of the general formula (II) is synthesized from the fluorinated α,β-unsaturated aldehyde obtained above. The synthesis is effected, for example, according to the process described in Carbohydrate Researches, 202 (1990), 177–191, in the following way:

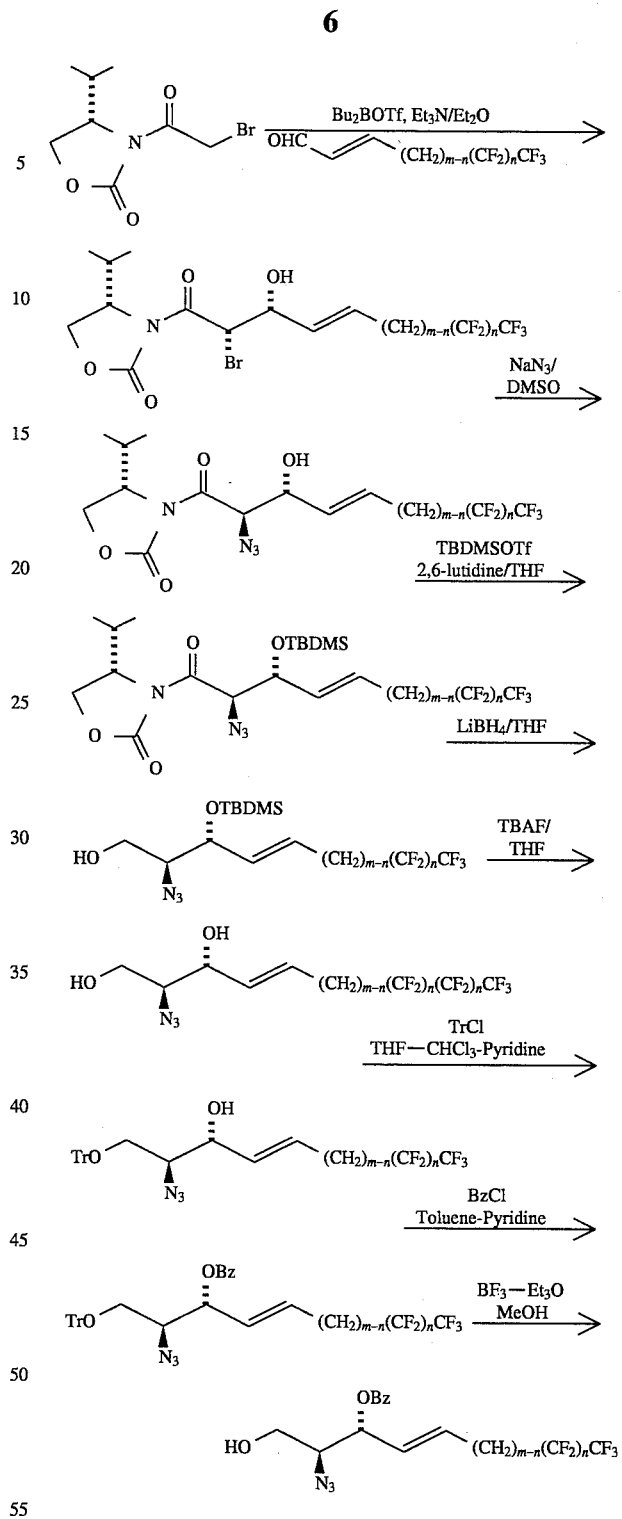

Notes:
Bu$_2$BOTf: di-(n-butyl)boron triflate
Et$_3$N: triethylamine
Et$_2$O: diethyl ether
TBDMSOTf: tert.-butyldimethylsilyl triflate
TBAF: tetrabutylammonium fluoride
TrCl: triphenylmethyl chloride
BzCl: benzoyl chloride Triethylamine and Bu$_2$BOTf are added to (4S)-3-bromoacetyl-4-isopropyl-2-oxazolidinone dissolved in anhydrous ether at a temperature of −78° C. The mixture is warmed to a room temperature and again cooled to −78° C.

The α,β-unsaturated aldehyde obtained above which was dissolved in an anhydrous ether is dropwise added to the mixture, followed by purification procedure, to obtain (4S)-3-[(2'S, 3'R,4'E)-2'-bromo-fluorinated-3'-hydroxy-4-(isopropyl)-4'-octadecenoyl]-2-oxazolidinone. The compound obtained is reacted with sodium azide in the presence of dimethyl sulfoxide to form an azide. The azide is reacted with 2,6-lutidine and TBDMSOTf at 0° C. in the presence of anhydrous THF, followed by the reaction with lithium boron hydride at 0° C. for 1.5 hours, to obtain (2S,3R,4E)-2-azide-3-O-tert.-butyldimethylsilyl-fluorinated-4-octadecene-1,3-diol. TBAF is reacted with the compound to obtain (2S,3R,4E)-2-azide-fluorinated-4-octadecene-1,3-diol in which a tert.-butyldimethylsilyl group is eliminated. The azide sphingosine obtained is reacted with TrCl in a THF-chloroform-pyridine mixed solvent to form a tritylated compound. It is reacted with BzCl in a pyridine-toluene mixed solvent to form a benzoylated compound. Finally, the trityl group therein is removed in methanol using $BF_3$-$Et_2O$ to obtain an intermediate, i.e., (2S,3R,4E)-2-azide-3-O-benzoyl-fluorinated-octadecene-1,3-diol.

Details of reaction conditions in every reaction are described in Examples 9 to 16, 24 to 31 and 41 to 48.

(3) Condensation of a GM3 saccharide chain portion with the fluorinated 2-azide sphingosine The fluorinated 2-azide sphingosine of the general formula (II) obtained above in which $R^4$ represents a protective group for a hydroxyl group and $R^5$ represents a hydrogen atom, is condensed with a GM3 saccharide chain portion of the general formula (VII):

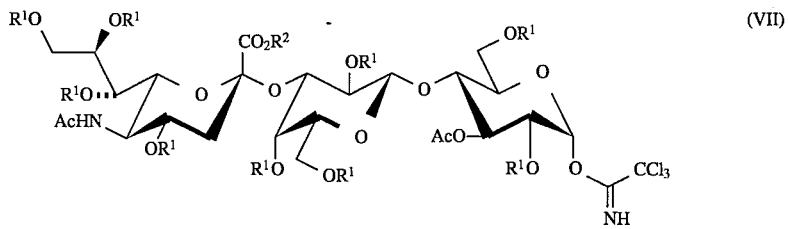

(VII)

in which $R^1$ represents a protective group for a hydroxyl group, and $R^2$ represents a protective group for a carboxylic acid group, to obtain a compound of the general formula (VIII):

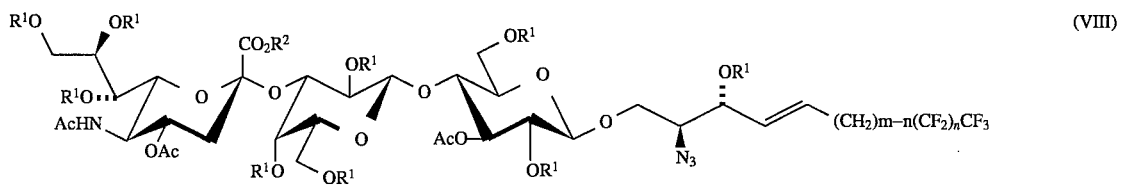

(VIII)

in which $R^1$, $R^2$, m and n are the same as defined above.

In the present invention, the protective groups for a hydroxy group include an acetyl group, a pivaloyl group, a benzoyl group and the like. The protective groups for a carboxylic acid group include an alkyl group such as a methyl group, an ethyl group, a n-propyl group, an isopropyl group, etc., a benzyl group optionally containing substituents (for example, a methyl, an ethoxy, and an acetoamide group) in the phenyl group, etc.

The compound of the general formula (VII) can be synthesized according to the process described in Japanese Patent Kokai No. 101691/1991. It is synthesized in the present invention as follows:

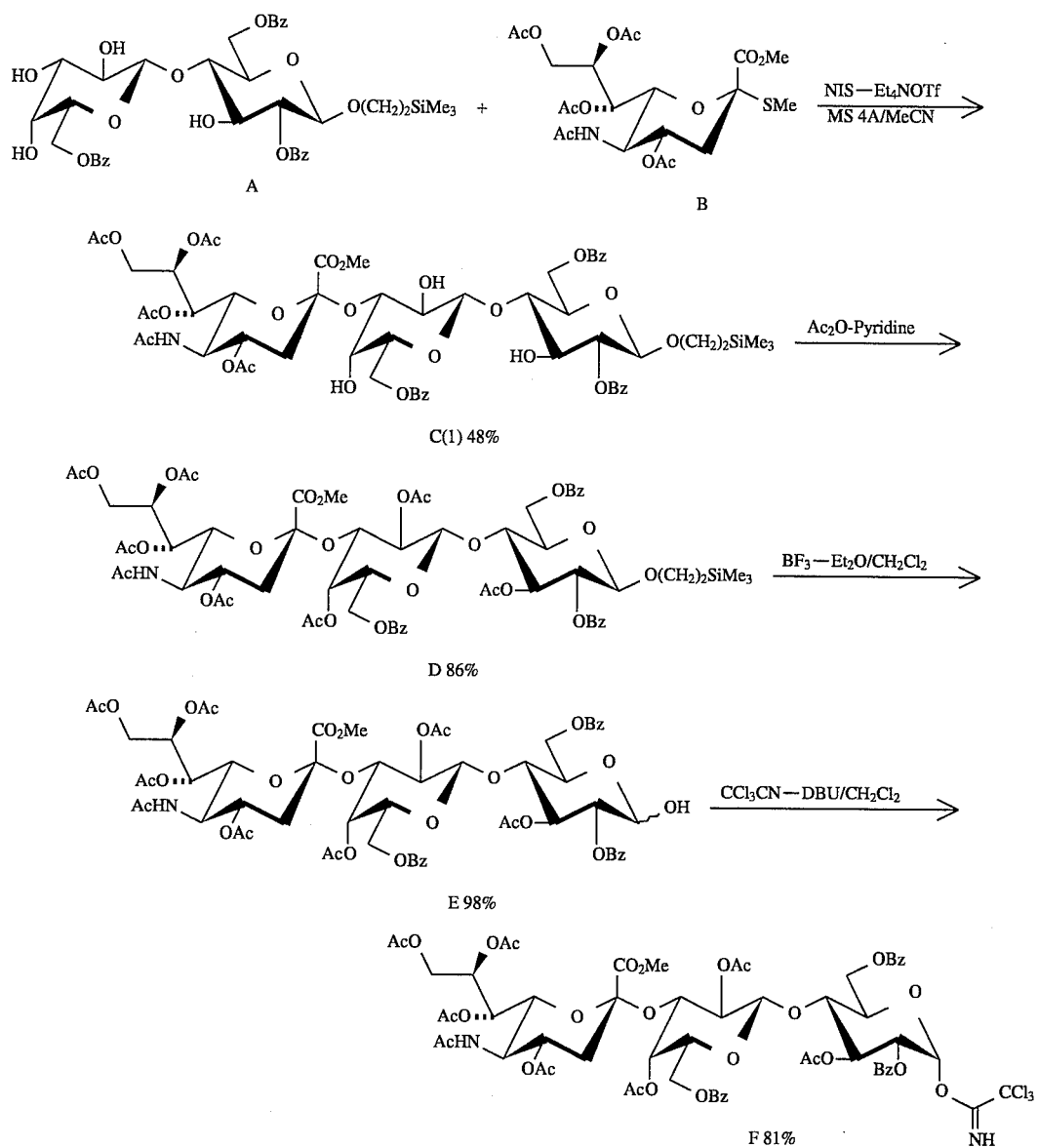

Notes:
NIS: N-iodosuccinimide
Et₄NOTf: tetraethylammonium triflate
MS4A: Molecular Sieve 4A
DBU: 1,8-diazabicyclo[5,4,0]undec-7-ene Condensation of the GM3 saccharide chain portion with the fluorinated azide sphingosine was carried out, for example, as follows: The compound of the general formula (11) and the compound of the general formula (VII) are dissolved in dichloromethane. Activated Molecular Sieve 4A is added to the mixture, followed by stirring under an argon atmosphere for 30 minutes. Then boron trifluoride-diethyl ether is dropwise added thereto under ice-cooling to react at 0° C. Details are described in Examples 17, 32 and 49.

(4) Reduction of an azide group in the condensed product into an amino group

An azide group in the condensed product of the general formula (VIII) is reduced to an amino group, for example, using a triphenylphosphine-water system, or a hydrogen sulfide-pyridine system, as described in Examples 18, 33, 50, 52 and 54 to obtain a compound of the general formula (IX):

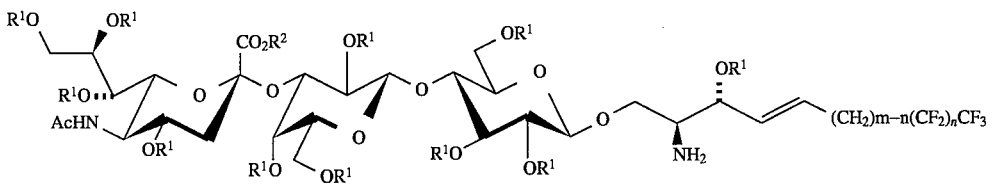 (IX)

in which $R^1$, $R^2$, m and n are the same as defined above.
(5) Condensation with a carboxylic acid The amino group of the compound of the general formula (IX) is condensed with a carboxyl group in a carboxylic acid of the general formula (X):

RCOOH  (X)

in which R represents an alkyl group or a fluoroalkyl group, using a dehydrating agent such as dicyclohexylcarbodiimde (DCC), diisopropylcarbodiimide (DIPC), N-ethyl-N'-3-dimethylaminopropylcarbodiimide (WSCI) to form an amide group to obtain a compound of the general formula (XI):

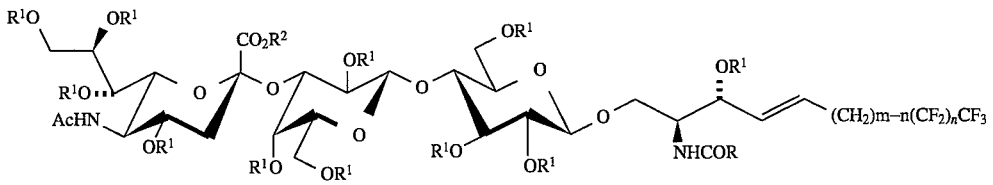 (XI)

in which $R^1$, $R^2$, R, m and n are the same as defined above.

A molar ratio of the compound of the general formula (IX) to the compound of the general formula (X) is in the range of 1:0.5 to 1:2.0, preferably in the range of 1:1 to 1:1.1. The dehydrating agent is used in an amount of 1 to 2 moles, preferably 1 to 1.1 moles per mole of the compound of the general formula (IX). Examples of preferred solvents are dichloromethane, chloroform, dichloroethane, dimethylformamide, etc. The reaction is usually carried out at a temperature of 15° to 25° C. After completion of the reaction, posttreatments such as extraction, distillation-off of solvent, etc. are effected and, if necessary, the product is purified by means of column chromatography.

Examples of the condensation reaction are described in Example 18, 33, 50, 52 and 54.
(6) Release of protective groups Protective groups of hydroxyl groups and a carboxyl group in the compound of the general formula (XI) are released to obtain a compound of the general formula (I):

temperature to 50° C. for a period of 30 minutes to 10 hours to release the protective groups of a hydroxyl groups. Then the protective group of a carboxylic group is released by cooling the mixture to 0° C., adding water thereto and stirring the resulting mixture at 0° C. for 1 to 6 hours. After removing salts therein with a cation-exchange resin (H+ type), column purification is effected, for example, using Sephadex LH-20 to obtain an ganglioside GM3 derivative of the general formula (I) which contains fluorine atoms in a ceramide portion thereof. Examples of the release of the protective groups are described in Examples 19, 34, 51, 53 and 55.

The present invention also relates to a process for bonding sialic acid with a saccharide chain portrion to synthesize a GM3 saccharide chain portion of the general formula (VII) which is used as a raw substance for synthesizing the compound of the general formula (I). That is, the present invention relates to a process for preparing a ganglioside GM3 intermediate, comprising the step of reacting a compound the general formula (IV):

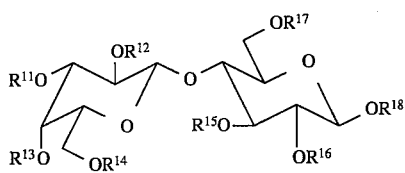 (IV)

in which $R^{11}$, $R^{12}$, $R^{13}$, $R^{14}$, $R^{15}$, $R^{16}$ and $R^{17}$ each represent a hydrogen atom or a protective group of a hydroxyl group and $R^{18}$ represents a trialkylsilylethyl group wherein the alkyl group contains 1 to 4 carbon atoms,

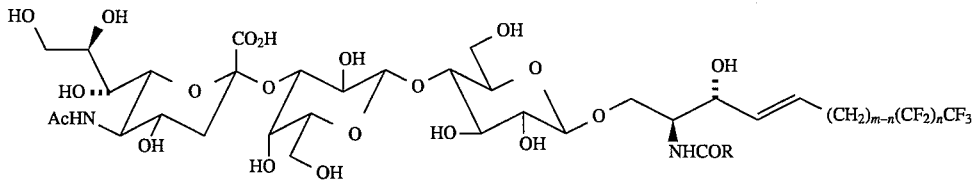 (I)

in which R, m and n are the same as defined above.

The release of the protective groups are, for example, effected as follows: The compound of the general formula (XI) is dissolved in anhydrous methanol, followed by addition of sodium methoxide in an amount of 2 to 4 equivalents per equivalent of the compound of the general formula (XI). The reaction mixture is reacted at a temperature of a room with a compound of the general formula (V):

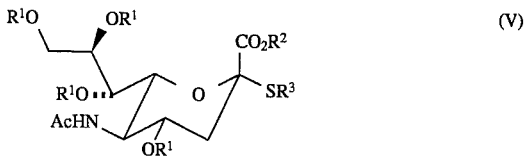

in which $R^1$ represents a protective group of a hydroxyl group, $R^2$ represents a protective group of a carboxyl group and $R^3$ represents an alkyl group containing 1 to 10 carbon atoms or a phenyl group optionally having substituents, in the presence of N-iodosuccinimide and trifluoromethanesulfonate to obtain a compound of the general formula (VI):

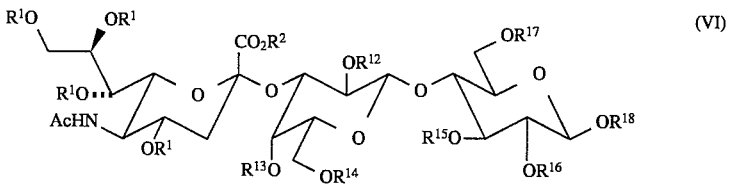

in which $R^1$ to $R^{18}$ are the same as defined above.

In the reaction, a molar ratio of the compound of the general formula (IV) to the compound of the general formula (V) is in the range of 1:3 to 2:1. N-iodosuccinimide is used in an amount of 1 to 10 equivalents per equivalent of the compound of the general formula (V). Examples of trifluoromethanesulfonates are tetramethylammonium, tetraethylammonium, tetrabutyulammonium, and triethylbenzylammonium thereof. The trifuoromethanesulfonate is used in amount of 0.01 to 0.5 equivalent per equivalent of N-iodosuccinimide. Examples of preferred solvents are acetonitrile, propionitrile, and the like. The reaction is preferably carried out at temperatures of −45° to −40° C.

For example, the compound of the general formula (IV) and the compound of the general formula (V) are dissolved in acetonitrile. Powdery Molecular Sieve 4A is then added to the solution in twice the total weight of the compounds of the general formulae (IV) and (V). Thereafter, the resulting suspension is stirred and then cooled to −45° C. N-iodosuccinimide and then trifluoromethanesulfonate are added thereto. The mixture is stirred under an argon atmosphere at temperatures of −45° to −40° C. for about 2 hours. An example of the reaction is shown in Example 1. Conventional processes are also shown in Comparative Examples 1 and 2.

EXAMPLES

The present invention will be illustrated by Examples, but is not limited thereto.

In Examples and Comparative Examples, abbreviation s used in NMR column are as follows: Me: methyl group, Ac: acetyl group, Ph: phenyl group Comparative Example 1

Synthesis of 2-(trimethylsilyl)ethyl-O-methyl-5-acetoamide-4,7,8,9-tetra-O-acetyl-3,5-dideoxy-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside) (referred to as "Compound (1)" hereinafter)

140 mg (0.268 mmol) of methyl(methyl-5-acetoamide-4,7,8,9-tetra-O-acetyl-3,5-dideoxy-2-thio-D-glycero-α-D-galacto-2-nonulopyranosylonate) (referred to as "Compound (B)" hereinafter) and 75 mg (0.1 mmol) of 2-(trimethylsilyl)ethyl-O-(6-O-benzoyl-β-D-galactopyranosyl)-(1→4)-2,6-di-O-benzoyl-β-D-glucopyranoside (referred to as "Compound (A)" hereinafter) were dissolved in 1 ml of acetonitrile under an argon atmosphere to form a solution. 150 mg of powdery Molecular Sieve 4A was then added thereto, followed by stirring for 16 hours. The resulting suspension was cooled to −30° C., followed by the addition of 200 mg of powdery Molecular Sieve 4A containing 245 mg of DMTST, and stirred under an argon atmosphere at around −20° C. for 24 hours. The reaction suspension was diluted with dichloromethane and then filtered. The filtrate was washed with an aqueous saturated sodium carbonate solution and then with water, dried over anhydrous sodium sulfate and then concentrated to obtain a syrup. It was subjected to column chromatography (a packing material: silica gel 60 (9385), an eluent: ethyl acetate/hexane=7/2) to obtain 5 mg of Compound (1). Yield: 4.1%. NMR(CDCl$_3$, δ lactose unit; 0.86(m, 2H), 3.58(m,1H), 4.40(d, J=8 Hz, 1H), 4.57(dd, J=12 Hz,5 Hz, 1H), 4.63(d, J=8 Hz, 1H), 4.73(dd, 1H 5.24(dd, J=9 Hz, 1H), 7.27–8.08 (m, 15H), sialic acid unit; 2.65(dd, 1H, J=13 Hz, 5 Hz), 3.80(s, 3H), 5.03(m, 1H), 5.70(d, 1 H, J=9 Hz)

Comparative Example 2

Synthesis of Compound (1)

140 mg (0.268 mmol) of the Compound (B) and 75 mg (0.1 mmol) of the Compound (A) were dissolved in 1.5 ml of anhydrous propionitrile under an argon atmosphere to form a solution. 370 mg of powdery Molecular Sieve 4A was then added thereto, followed by stirring for 16 hours. The resulting suspension was cooled to −55° C., before 48 mg (0.270 mmol) of N-bromosuccinimide and then 20 mg (0.051 mmol) of tetrabutylammonium triflate were added. The suspension was stirred under an argon atmosphere at temperatures of −55° to −40° C. for 3.5 hours. The reaction suspension was diluted with dichloromethane and then filtered. The filtrate was washed with an aqueous saturated sodium bicarbonate solution and then with water, dried over anhydrous sodium sulfate and then concentrated to obtain a syrup. It was subjected to column chromatography (a packing material: silica gel 60 (9385), an eluent: ethyl acetate/hexane=7/2). The fractions containing the Compound (A) were collected and concentrated under a reduced pressure to obtain a residue, which was subjected to a column chromatography (a packing material: Wako gel C-200, an eluent: methanol/dichloromethane=1/5→1/20) to recover 70 mg of the Compound (A). Recovery ratio: 93.3%.

Example 1

Synthesis of Compound (1)

728 mg (1.40 mmol) of the Compound (B) and 460 mg (0.61 mmol) of the Compound (A) were dissolved in 6 ml of anhydrous acetonitrile under an argon atmosphere to form a solution. 2.4 g of powdery Molecular Sieve 4A was then added thereto, followed by stirring for 16 hours. The resulting suspension was cooled to −45° C., followed by the addition of 820 mg (3.65 mmol) of N-iodosuccinimide and then 140 mg (0.358 mmol) of tetrabutylammonium triflate, and stirred under an argon atmosphere at temperatures of −45° to −40° C. for 2 hours. The reaction suspension was diluted with dichloromethane and then filtered. The filtrate was washed with an aqueous saturated sodium carbonate solution and then with water, dried over anhydrous sodium sulfate and then concentrated to obtain a syrup. It was subjected to column chromatography (a packing material: silica gel 60 (9385), an eluent: ethyl acetate/hexane=7/2) to obtain 360 mg of the Compound (1). Yield: 48.0%.

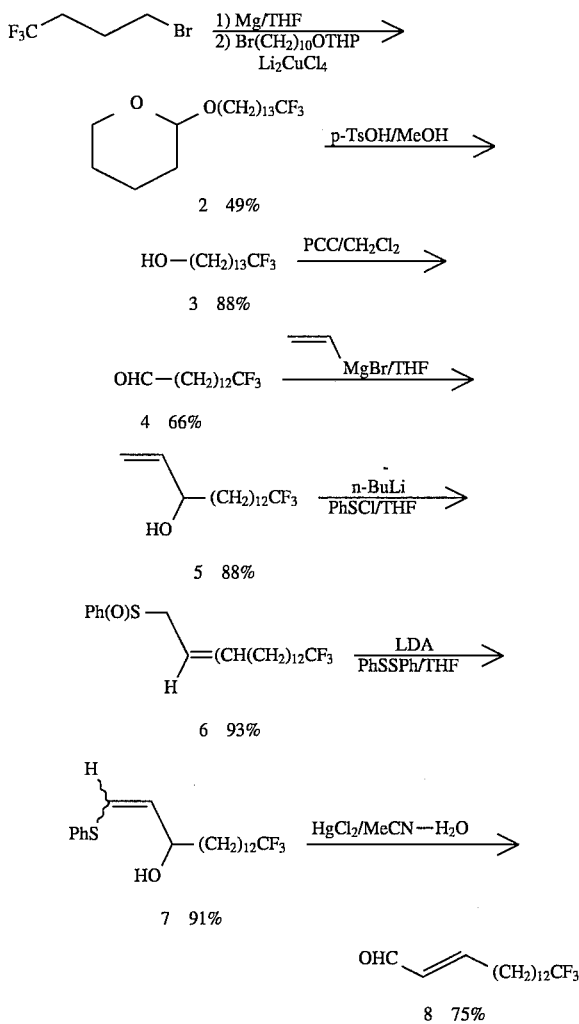

Example 2

Synthesis of 14,14,14-trifluoro-1-[(3,4,5,6-tetrahydro-2H-pyrane-2-yl)oxy]tetradecane (referred to as "Compound (2)" hereinafter)

0.3 g (1.57 mmol) of 4,4,4-trifluorobromobutane was added under an argon atmosphere to 0.39 g (16.0 mmol) of magnesium in a form of flakes and a piece of iodine which had been suspended in 10 ml of tetrahydrofuran. After stirring for 3 minutes, the temperature of the reaction mixture was elevated and its color due to iodine disappeared. 2.9 g (16.4 mmol) of 4,4,4-trifluorobromobutane dissolved in 13 ml of anhydrous tetrahydrofuran was dropwise added under mild reflux. After the completion of dropwise addition, the reaction mixture was refluxed for 30 minutes to obtain a solution, which was cooled to a room temperature. The reaction solution was dropwise added to 3.2 g (10.0 mmol) of 10-bromo-1-[(3,4,5,6-tetrahydro-2H-pyrane-2-yl)oxy]tetradecane dissolved in 15 ml of anhydrous tetrahydrofuran which had been cooled to −78° C. After 6 ml (0.6 mmol) of 0.1 M dilithium tetrachlorocuplate in tetrahydrofuran was added at −78° C., the reaction mixture was warmed to a room temperature over 3 hours and further stirred for 20 hours. The reaction mixture was poured into an aqueous 1 M ammonium chloride solution and then extracted with ether. The ether layer was washed with an aqueous saturated sodium chloride solution, dried over anhydrous magnesium sulfate and concentrated under a reduced pressure to obtain a residue, which was subjected to flash column chromatography (a packing material: silica gel 60K230, an eluent: ether/hexane=1/19) to obtain 1.73 g of Compound (2). Yield: 49.1%. NMR(CDCl$_3$,TMS): δ 4.58(m, 1H, O-CH-O), 3.9–3.2(m, 4H, CH$_2$O), 2.2–1.9(m, 2H, CF$_3$CH$_2$), 1.85–1.1(m, 28H, 14×CH$_2$) $^{19}$F-NMR(CDCl$_3$, CFCl$_3$): δ −66.79(t, J=11 Hz, 3F, CF$_3$)

Example 3

Synthesis of 14,14,14-trifluoro-1-tetradecanol (referred to as "Compound (3)" hereinafter)

5.25 g (14.89 mmol) of the Compound (2) was dissolved in 100 ml of methanol to form a solution. 0.28 g (1.47 mmol) of p-toluenesulfonic acid monohydrate was added thereto to obtain a reaction mixture, which was stirred at a room temperature for 2 hours. After the solvent was distilled off under a reduced pressure, the residue obtained was dissolved in ether to form a solution. It was washed with an aqueous saturated sodium bicarbonate solution and then with an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/5) to obtain 3.50 g of Compound (3). Yield: 87.6%. It was recrystallized from ethanol-water to obtain a needle crystal.

m.p. 46.5°–47.0° C. NMR(CDCl$_3$,TMS): δ 3.65 (t, J=6 Hz, 2H, CH$_2$—O), 2.2–1.9 (m, 2H, CF$_3$CH$_2$) 1.7–1.1(m, 23H, 11×CH$_2$+OH.)

Example 4

Synthesis of 14,14,14-trifluoro-1-tetradecanal (referred to as "Compound (4)" hereinafter)

153 mg (0.710 mmol) of the Compound (3) which had been dissolved in 2.5 ml of dichloromethane was added to 107 mg (0.399 mmol) of pyridinium chlorochromate dissolved in 1 ml of dichloromethane to obtain a reaction mixture. It was stirred at a room temperature for 8 hours, diluted with ether and filtered using Celite. The filtrate was subjected to distillation to obtain a residue. It was purified by flash column chromatography (a packing material: silica gel 60K230, an eluent: ethyl acetate/hexane=1/10) to obtain 70 mg of Compound (4). Yield: 66.0%.

NMR(CDCl$_3$,TMS): δ 9.77(t, J=2 Hz, 1H, CHO), 2.42(dt, J=7 Hz,2 Hz,2H,CH$_2$CHO), 2.2–1.9(m, 2H, CF$_3$CH$_2$), 1.8–1.1(m, 20H, 10×CH$_2$) $^{19}$F-NMR(CDCl$_3$, CFCl$_3$): δ −66.79(t, J=11 Hz, 3F, CF$_3$)

Example 5

Synthesis of 16,16,16-trifluoro-3-hydroxy-1-hexadecene (referred to as "Compound (5)" hereinafter)

60 mg (0.225 mmol) of the Compound (4) was dissolved in 1 ml of anhydrous tetrahydrofuran under an argon atmosphere to form a solution. The solution was dropwise added to 0.4 ml (0.4 mmol) of 1 M vinyl bromide magnesium in tetrahydrofuran under ice water-cooling (about 5° C.). After the completion of the dropwise addition, the reaction mixture was warmed to a room temperature, stirred at a room temperature for 30 minutes, and again cooled with ice water. The reaction mixture was treated with an aqueous saturated ammonium chloride solution, followed by extraction with ether. An organic layer was washed with an aqueous saturated sodium chloride solution, dried over anhydrous magnesium sulfate and concentrated under a reduced pressure to obtain a residue. It was then subjected to flash column chromatography (a packing material: silica gel 60K230, an eluent: ethyl acetate/hexane=1/10) to obtain 58 mg of Compound (5). Yield: 87.5%.

NMR(CDCl$_3$,TMS): δ 5.87(ddd, J=17 Hz,10 Hz,6 Hz, 1H, —CH=C), 5.16(m, 2H, C=CH$_2$), 4.10(q, J=7 Hz, 1H, CH—(OH)), 2.2–1.9(m, 2H, CF$_3$CH$_2$), 1.8–1.1(m,23H, 11×CH$_2$.+OH)

Example 6

Synthesis of 1-[(2E)-16,16,16-trifluoro-2-hexadecenyl]phenyl sulfoxide (referred to as "Compound (6)" hereinafter)

1.33 g (4.52 mmol) of the Compound (5) was dissolved in 20 ml of anhydrous tetrahydrofuran under an argon atmosphere to form a solution. 3.1 ml (4.53 mmol) of 1.46 M butyl lithium in hexane was dropwise added thereto at −20° C., followed by addition of 0.70 g (4.84 mmol) of benzenesulfenyl chloride dissolved in 1 ml of anhydrous tetrahydrofuran at −20° C. After the reaction mixture was warmed to a room temperature, it was stirred for 15 minutes and concentrated under a reduced pressure to obtain a residue. it was diluted with ether before it was washed with an aqueous saturated sodium chloride solution, dried over anhydrous magnesium sulfate and concentrated under a reduced pressure to obtain a residue. It was then subjected to flash column chromatography (a packing material: silica gel 60K230, an eluent: ether/hexane=2/3) to obtain 1.69 g of Compound (6). Yield: 92.9%.

m.p. 44.5°–46.0° C. NMR(CDCl$_3$,TMS): δ 7.65–7.40(m, 5H, aromatic), 5.56(dt, J=15 Hz, 6 Hz, 1H, C=CHCH$_2$S), 5.27(dt, J=15 Hz, 7 Hz, 1H, C—CH$_2$CH=CH—), 3.49(d, J=7 Hz, 2H, CH$_2$—S(O)Ph), 2.2–1.9(m, 4H, CF$_3$CH$_2$+C—CH$_2$—CH=CH), 1.7–1.1(m, 20H, 10×CH$_2$)

Example 7

Synthesis of (16,16,16-trifluoro-3-hydroxy-1-hexadecenyl)phenyl sulfide (referred to as "Compound (7)" hereinafter)

0.67 ml (3.84 mmol) of diisobutylamine was added to 10 ml of anhydrous tetrahydrofuran under an argon atmosphere to form a mixture. 2.65 ml (3.87 mmol) of 1.46 M butyl lithium in hexane was dropwise added thereto at −78° C. After stirring of the resulting mixture at −78° C., 1.33 g (4.52 mmol) of the Compound (6) in 1.5 ml of anhydrous tetrahydrofuran was added at a stroke thereto. The resulting mixture was stirred at −78° C. for 1 hour and then at temperatures of −65° to −60° C. for 1 hour before it was again cooled to −78° C. The mixture was added through a cannula to 0.92 g (4.21 mmol) of diphenyl disulfide dissolved in 6 ml of anhydrous tetrahydrofuran which had been cooled to 0° C. After the mixture was stirred at 0° C. for 1 hour, it was poured into 70 ml of an aqueous 10% hydrochloride solution and then extracted with chloroform. An organic layer was washed with an aqueous saturated sodium bicarbonate solution, dried over anhydrous magnesium sulfate and concentrated under a reduced pressure, to obtain a brown oily residue. It was immediately subjected to flash column chromatography (a packing material: silica gel 60K230, an eluent: ethyl acetate/hexane=1/9) to obtain 1.28 g of Compound (7). Yield:90.6%.

NMR(CDCl$_3$,TMS): δ 7.5–7.1(m, 5H, aromatic), 6.42(d, J=16 Hz, 1H, C=CHPh), 5.86(dd, J=16 Hz, 7 Hz, 1H, —CH=C—SPh), 4.17(q, J=7 Hz, 1H, CH(OH)), 2.2–1.9(m, 2H, CF$_3$CH$_2$), 1.7–1.1(m, 23H, 11×CH$_2$+OH)

Example 8

Synthesis of 16,16,16-trifluoro-trans-2-hexadecenal (referred to as "Compound (8)" hereinafter)

1.27 g (3.15 mmol) of the Compound (7) was dissolved in a mixed solvent of 25 ml of acetonitrile and 5 ml of water to form a solution, to which 0.901 g (3.32 mmol) of mercury chloride (II) was added. The resulting reaction mixture was stirred at temperatures of 40° to 50° C. for 15 hours, and spontaneously cooled to a room temperature before it was filtered using Celite. Undissolved portions were washed with chloroform and the filtrate and the washing liquid were combined. The combined liquid was washed with an aqueous 10% sodium bicarbonate solution. A water layer was extracted with chloroform. Organic layers which were combined were dried over anhydrous magnesium sulfate and concentrated under a reduced pressure to obtain a residue. It was subjected to flash column chromatography (a packing material: silica gel 60K230, an eluent: ether/hexane=1/10) to obtain 0.61 g of Compound (8). Yield: 74.8%.

NMR(CDCl$_3$,TMS): δ 9.51(d, J=8 Hz, 1H, —CHO), 6.86(dt, J=16 Hz,7 Hz, 1H, CH$_2$CH=CH), 6.12(dd, J=16 Hz,8 Hz, 1H, C=CH—CHO), 2.34(dt, J=7 Hz, 7 Hz, 2H, CH$_2$—CH=C), 2.2–1.9(m, 2H, CF$_3$CH$_2$), 1.7–1.1(m, 20H, 10×CH$_2$)

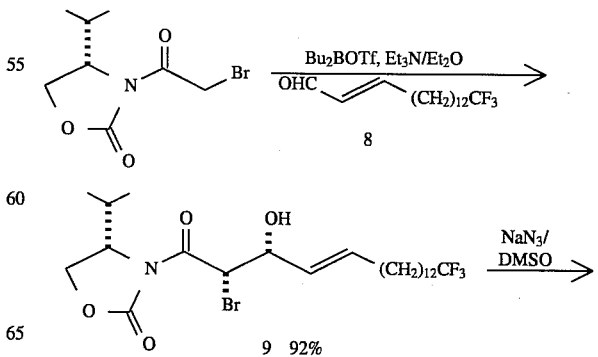

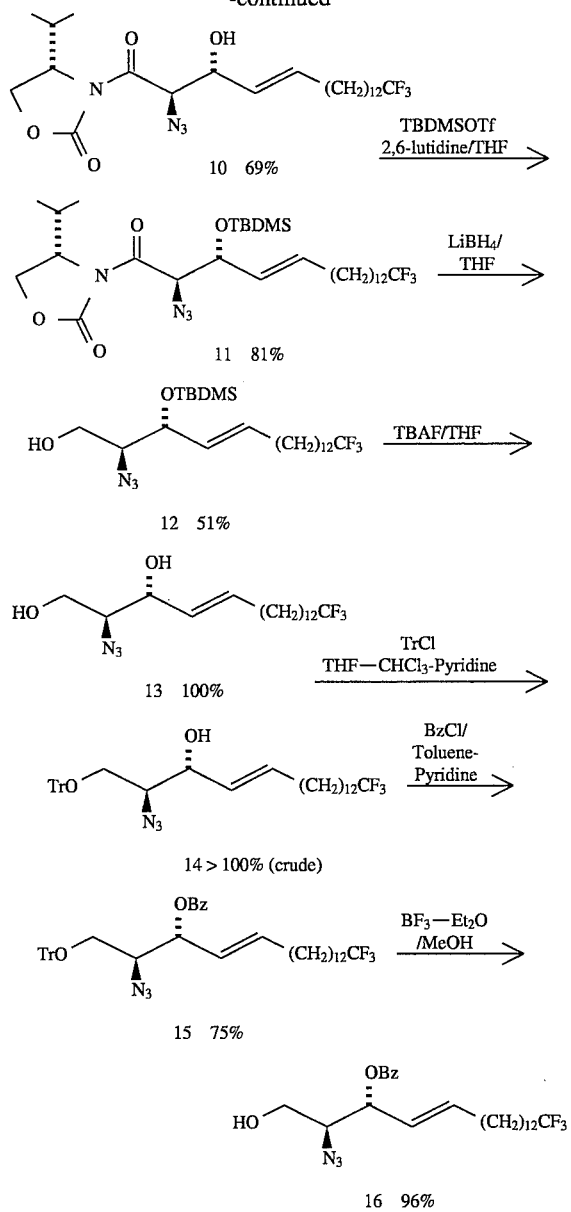

dropwise added thereto. The resulting mixture was stirred at −78° C. for 45 minutes and then at 0° C. for 1.5 hours before it was diluted with 80 ml of ether. The resulting mixture was poured into 70 ml of an aqueous 1 M sodium hydrogensulfate solution. An organic layer was taken, washed with 30 ml of an aqueous 1 M sodium hydrogensufate solution and then with an aqueous saturated sodium chloride solution and concentrated under a reduced pressure to obtain a residue. It was again dissolved in 11 ml of ether and cooled to 0° C. A solution of 5.5 ml of methanol and 5.5 ml of an aqueous 30% hydrogen peroxide solution was gradually dropwise added thereto and the resulting reaction mixture was stirred at 0° C. for 1 hour. The reaction mixture was diluted with 30 ml of ether and washed with an aqueous saturated sodium bicarbonate solution before a water layer was twice extracted with 20 ml of ether. Organic layers were combined, washed with 30 ml of an aqueous saturated sodium bicarbonate solution and then with 20 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/4) to obtain 1.02 g of Compound (9). Yield:91.6%.

m.p. 42.5°–43.2° C. $[\alpha]_D^{22}$ +51.9° (c 0.268, $CHCl_3$) NMR($CDCl_3$,TMS): δ 5.85(dt, J=16 Hz, 7 Hz, 1H, CH=CH—$CH_2$), 5.68(d, J=5 Hz, 1H, CHBr), 5.47(dd, J=16 Hz,7 Hz, 1H, CH=CH—$CH_2$), 4.6–4.2(m, 4H, $CH_2$—O, CH—O, CH—NCO), 3.15(d, J=1 Hz, 1H, OH), 2.41 (m, 1H, $CHMe_2$), 2.2–1.9(m, 4H, $CF_3CH_2$, C=C—$CH_2$), 1.7–1.1(m, 20H, 10×$CH_2$), 0.95(d, J=7 Hz, 6H, 2×$CH_3$)

Example 10

Synthesis of
(4S)-3-[(2'R,3'R,4'E)-2'-azide-18',18',18'-trifluoro-3'-hydroxy-4-(isopropyl)-4'-octadecenoyl]-2-oxazolidinone (referred to as "Compound (10)" hereinafter)

1.02 g (1.88 mmol) of the Compound (9) was dissolved in 5 ml of dimethylsulfoxide to form a solution, to which 0.25 g (3.85 mmol) of sodium azide was added at a room temperture to obtain a reaction mixture. The mixture was stirred at the room temperature for 2 hours before it was diluted with 30 ml of ether, washed three times with 10 ml of water and then with 10 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/4) to obtain 0.65 g of Compound (10). Yield: 68.5%.

m.p. 29.0°–31.5° C. $[\alpha]_D^{22}$ +21.4° (c 2.285, $CHCl_3$) NMR($CDCl_3$,TMS): δ 5.89(dt, J=16 Hz, 7 Hz, 1H, CH=CH—$CH_2$), 5.61 (dd, J=16 Hz, 7 Hz, 1H, CH=CH—$CH_2$), 5.10(d, J=8 Hz, 1H, $CHN_3$), 4.6–4.2(m, 4H $CH_2$—O, CH—O, CH—NCO), 2.6–2.25(m, 2H, $CHMe_2$, OH), 2.2–1.9(m, 4H, $CF_3CH_2$, C=C—$H_2$), 1.7–1.1(m, 20H, 10×$CH_2$), 0.90(d, J=7 Hz, 6H, 2×$CH_3$)

Example 11

Synthesis of
(4S)-3-[(2'R,3'R,4'E)-2'-azide-3'-O-tert.-butyldimethylsilyl-18',18',18'-trifluoro-3'-hydroxy-4-(isopropyl)-4'-octadecenoyl]-2-oxazolidinone (referred to as "Compound (11)" hereinafter)

0.65 g (1.29 mmol) of the Compound (10) dissolved in 7 ml of anhydrous terahydrofuran was cooled to 0° C. under Example 9

Synthesis of
(4S)-3-[(2'S,3'R,4'E)-2'-bromo-18',18',18',-trifluoro-3'-hydroxy-4-(isopropyl)-4'-octadecenoyl-2-oxazolidinone (referred to as "Compound (9)" hereinafter)

0.65 ml (4.67 mmol) of triethylamine was added to 0.821 g (3.28 mmol) of (4S)-3-(bromoacetyl)-4-(isopropyl)-2-oxazolidinone dissolved in 11 ml of anhydrous ether at −78° C. under an argon atmosphere to form a mixture. After stirring for 5 minutes, 0.85 ml (3.38 mmol) of di-(n-butyl)boron triflate was slowly dropwise added thereto. After the reaction mixture was stirred at −78° C. for 15 minutes, refrigerants were removed and the mixture was stirred at a room temperature for 2 hours. The reaction mixture was again cooled to −78° C. gradually before 0.60 g (2.05 mmol) of the Compound (8) dissolved in 10 ml of anhydrous ether was an argon atmosphere. 0.3 ml (2.58 mmol) of 2,6-lutidine was then added, followed by addition of 0.45 ml (1.96 mmol) of tert.-butyldimethylsilyl triflate to obtain a reaction mixture. It was stirred at 0° C. for 30 minutes and then at a room temperature for 1 hour. It was then diluted with 25 ml of ethyl acetate, washed with 10 ml of water and then with 10 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/6) to obtain 0.648 g of Compound (11). Yield: 81.1%.

$[\alpha]_D^{22}$ −1.60° (c 4.03, CHCl$_3$) NMR(CDCl$_3$,TMS): δ 5.74(dt, J=15 Hz, 7 Hz, 1H, CH=CH—CH$_2$), 5.52(dd, J=15 Hz, 7 Hz, 1H, CH=CH—CH$_2$), 5.22(d, J=7 Hz, 1H, CHN$_3$), 4.63(dd, J=7 Hz, 7 Hz, 1H, CHOSi), 4.49(m, 1H, CH—NCO), 4.4–4.2(m, 2H, CH$_2$—O), 2.3(m, 1H, CHMe$_2$), 2.2–1.9(m, 4H, CF$_3$CH$_2$, C=C—CH$_2$), 1.7–1.1(m, 20H, 10×CH$_2$), 0.95–0.8(m, 15H, 2×CH$_3$, SiCMe$_3$), 0.08(s, 3H, SiCH$_3$), 0.06(s, 3H, SiCH$_3$)

Example 12

Synthesis of (2S,3R,4E)-2'-azide-3-O-tert.-butyldimethylsilyl-18,18,18-trifluoro-4-octadecene-1,3-diol (referred to as "Compound (12)" hereinafter)

648 mg (1.28 mmol) of the Compound (11) dissolved in 7 ml of anhydrous terahydrofuran was cooled to 0° C. under an argon atmosphere. 85 mg (3.90 mmol) of lithium boron hydride was then added in three portions. The resulting mixture was stirred at 0° C. for 1.5 hours and then at a room temperature for 30 minutes, and again cooled to 0° C. It was diluted with 10 ml of ethyl acetate before 10 ml of an aqueous saturated ammonium chloride solution was gradually added thereto in order to decompose excessive lithium boron hydride. An organic layer was taken and a water layer was extracted with ethyl acetate. The organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/8) to obtain 320 mg of Compound (12). Yield: 50.5%.

$[\alpha]_D^{22}$ −36.6° (c 4.51, CHCl$_3$) NMR(CDCl$_3$,TMS): δ 5.70(dt, J=15 Hz, 7 Hz, 1H, CH=CH—CH$_2$), 5.45(dd, J=15 Hz, 7 Hz, 1H, CH=CH—CH$_2$), 4.22(dd, J=7 Hz, 5 Hz, 1 H, CHOSi), 3.8–3.6(m, 2H, CH$_2$—OH), 3.41(ddd, 1H, CHN$_3$), 2.2–1.9(m, 5H, CF$_3$CH$_2$, C=C—CH$_2$, OH), 1.7–1.1(m, 20H, 10×CH$_2$), 0.90(s, 9H, SiCMe$_3$), 0.09(s, 3H, SiCH$_3$), 0.05(s, 3H, SiCH$_3$) $^{19}$F-NMR(CDCl$_3$,CFCl$_3$): δ −66.79(t, J=11 Hz, 3F, CF$_3$)

Example 13

Synthesis of (2S,3R,4E)-2-azide-18,18,18-trifluoro-4-octadecene-1,3-diol (referred to as "Compound (13)" hereinafter)

320 mg (0.648 mmol) of the Compound (12) dissolved in 6 ml of anhydrous terahydrofuran was cooled to 0° C. under an argon atmosphere. 1.0 ml (1.0 mmol) of 1.0 M tetrabutylammonium fluoride in tetrahydrofuran was then dropwise added. The resulting mixture was stirred at a room temperature for 1 hour. It was diluted with 200 ml of ethyl acetate, washed with water (50 ml×2) and then with 50 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/3) to obtain 255 mg of Compound (13). Yield: 100%.

$[\alpha]_D^{25}$ −28.9° (c 4.03, CHCl$_3$) NMR(CDCl$_3$,TMS): δ 5.83(dt, J=16 Hz, 7 Hz, 1H, CH=CH—CH$_2$), 5.54(dd, J=16 Hz, 7 Hz, 1H, CH=CH—CH$_2$), 4.25(m, 1H, CHOH), 3.85–3.65(m, 2H, CH$_2$—OH), 3.51(dt, J=5 Hz, 5 Hz, 1H, CHN$_3$), 2.2–1.9(m, 5H, CF$_3$CH$_2$, C=C—CH$_2$, OH), 1.7–1.1(m, 21H, 10×CH$_2$, OH)

Example 14

Synthesis of (2S,3R,4E)-2-azide-18,18,18-trifluoro-1-triphenylmethoxy-4-octadecene-3-ol (referred to as "Compound (14)" hereinafter)

250 mg (0.629 mmol) of the Compound (13) was dissolved in a mixed solvent of anhydrous terahydrofuran-chloroform-pyridine (0.8 ml, 0.8 ml, 0.8 ml) under an argon atmosphere to form a solution. 240 mg (0.861 mmol) of triphenylmethyl chloride was added thereto at 0° C. The resulting mixture was stirred at a room temperature for 50 hours and concentrated under a reduced pressure to obtain a residue. It was dissolved in ether and was washed with an aqueous saturated sodium bicarbonate solution. A water layer was extracted twice with 20 ml of ether. Organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/8) to obtain 420 mg of crude Compound (14). Yield: >100%.

NMR(CDCl$_3$,TMS): δ 7.6–7.15(m, 15H, 3×Ph), 5.66(dt, J=15 Hz, 7 Hz, 1H, CH=CH—CH$_2$), 5.32(dd, J=15 Hz, 7 Hz, 1H, CH=CH—CH$_2$), 4.20(m, 1H, CHOH), 3.50(dt, J=5 Hz, 5 Hz, 1H, CHN$_3$), 3.30(d, J=5 Hz, 2H, CH$_2$—OTr), 2.2–1.9(m, 5H, CF$_3$CH$_2$, C=C—CH$_2$, OH), 1.7–1.1(m, 20H, 10×CH$_2$)

Example 15

Synthesis of (2S,3R,4E)-2-azide-3-benzoyloxy-18,18,18-trifluoro-1-triphenylmethoxy-4-octadecene (referred to as "Compound (15)" hereinafter)

420 mg (0.676 mmol) of the crude Compound (14) was dissolved in a mixed solvent of 2 ml of anhydrous toluene and 0.5 ml of pyridine to form a solution. 0.18 ml (1.55 mmol) of benzoyl chloride was added thereto at 0° C. The mixture was warmed to a room temperature, and stirred for 3 hours. It was poured into ice-cooled water and extracted with ether. An organic layer was dried over anhydrous magnesium sulfate and concentrated under a reduced pressure to obtain a residue. It was subjected to flash column chromatography (a packing material: silica gel 60K230, an eluent: ethyl acetate/hexane=1/20) to obtain 360 mg of Compound (15). Yield: 75.3%.

$[\alpha]_D^{23}$ −15.2° (c 7.11, CHCl$_3$) NMR(CDCl$_3$,TMS): δ 8.1–7.1(m, 20H, 4×Ph), 5.82(dt, J=15 Hz, 7 Hz, 1H, CH=CH—CH$_2$), 5.63(dd, J=9 Hz, 5 Hz, 1H, CHOBz), 5.42(dd, J=15 Hz, 7 Hz, 1H, CH=CH—CH$_2$), 3.86(dt, J=6 Hz, 5 Hz, 1H, CHN$_3$), 3.29 and 3.20(dd and dd, 2H, CH$_2$—OTr), 2.2–1.9(m, 4H, CF$_3$CH$_2$, C=C—CH$_2$), 1.7–1.1(m, 20H, 10×CH$_2$)

Example 16

Synthesis of (2S,3R,4E)-2-azide-3-benzoyloxy-18,18,18-trifluoro-4-octadecene-1-ol (referred to as "Compound (16)" hereinafter)

To 360 mg (0.496 mmol) of the Compound (15) dissolved in a mixed solvent of 1.8 ml of anhydrous toluene and 1.2 ml of anhydrous methanol, 83 ml (0.675 mmol) of boron trifluoride-diethyl ether complex was dropwise added at 0° C. under an argon atmosphere. The reaction mixture was stirred at a room temperature for 11 hours, poured into an aqueous saturated sodium bicarbonate solution which had been cooled with ice, and extracted with ether. An organic layer was dried over anhydrous magnesium sulfate and concentrated under a reduced pressure to obtain a residue. It was subjected to flash column chromatography (a packing material: silica gel 60K230, an eluent: ethyl acetate/hexane= 1/5) to obtain 229 mg of Compound (16). Yield: 95.5%.

$[\alpha]_D^{25}$ −42.0° (c 4.04, CHCl$_3$) NMR(CDCl$_3$,TMS): δ 8.1–7.4(m, 5H, Ph), 6.1–5.8(m, 1H, CH=CH—CH$_2$), 5.7–5.5(m, 2H, CHOBz, CH=CH—CH$_2$), 3.8–3.5(2m, 3H, CHN$_3$, CH$_2$—OH), 2.2–1.7(m, 5H, CF$_3$CH$_2$, C=C—CH$_2$, OH), 1.6–1.1(m, 20H, 10×CH$_2$)

Example 17

Synthesis of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azide-3-O-benzoyl-18,18,18-trifluoro-4-octadecene-1,3-diol (referred to as "Compound (17)" hereinafter)

289 mg (0.207 mmol) of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyl trichloroacetoimidate and 200 mg (0.414 mmol) of the Compound (16) were dissolved in 6 ml of anhydrous dichloromethane under an argon atmosphere to form a solution. 3.45 g of Molecular Sieve 4A was added thereto. The mixture was stirred at a room temperature for 30 minutes. It was cooled to 0° C. before 60 mg (0.423 mmol) of boron trifluoride-diethyl ether complex was added. The reaction mixture was stirred at 0° C. for 4 hours. It was filtered using Celite and undissolved portions were washed with dichloromethane. The filtrate and the washing liquid were combined, washed with an aqueous 1 M sodium bicarbonate solution and then with water, dried over

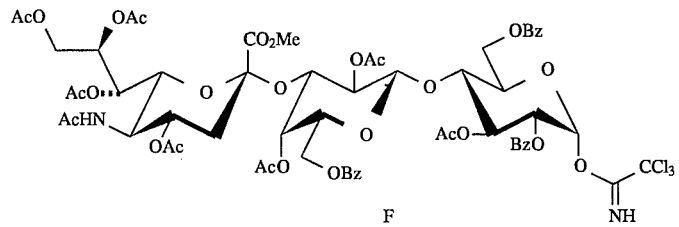
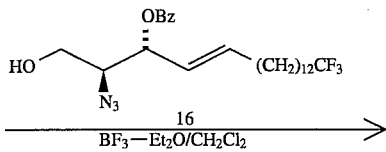
F

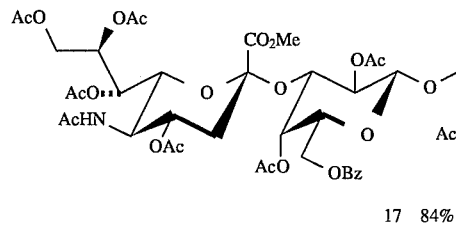
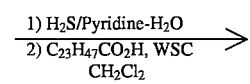
17  84%

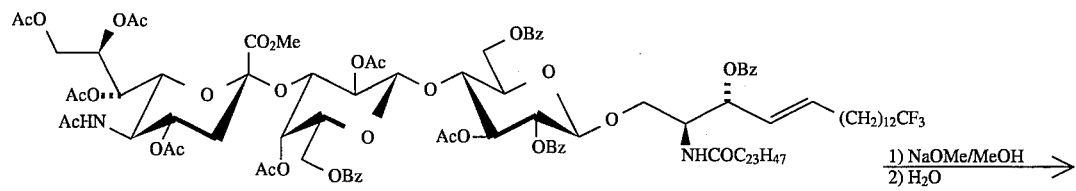
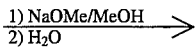
18  72%

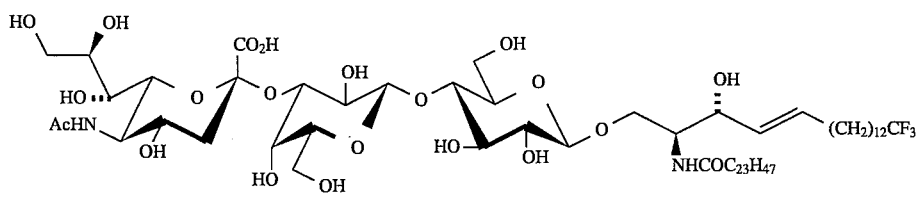
19  76% anhydrous magnesium sulfate and concentrated under a reduced pressure to obtain a residue. It was subjected to flash column chromatography (a packing material: silica gel 60K230, an eluent: ethyl acetate/hexane=3/1) to obtain 300 mg of Compound (17). Yield: 84.4%.

$[\alpha]_D^{25}$ −2.49° (c 0.59, CHCl$_3$) IRmax(KBr)(cm$^{-1}$): 3390(NH), 2110(N$_3$), 1740,1230 (ester), 1690,1540 (amide), 710 (phenyl) NMR(CDCl$_3$,TMS): lactose unit; δ 4.60 (dd, J=10 Hz, 3 Hz, 1H, H-3'), 4.68(d, J=8 Hz, 1H, H-1), 4.88(d, J=8 Hz, 1H, H-1'), 5.00(d, 1H, H-4'), 5.05(d, 1H, J=10 Hz, H-2') 5.25(dd, J=9 Hz, 1H, H-2), 7.3–8.1 (m, 20H, 4×Ph), sialic acid unit; δ 1.66 (dd, J=13 Hz, 13 Hz, 1H, H-3a), 1.84(s, 3H, N—COCH$_3$), 2.58(dd, J=13 Hz, 5 Hz, 1H, H-3e), 3.71(s, 3H, OCH3), 4.86(m, 1H, H-4), ceramide unit; δ 5.67(dt, J=13 Hz, 7 Hz, 1H, H-5), O-acetyl group; δ 1.98, 2.00, 2.01, 2.02, 2.03, 2.11, 2.20(7s, 21H, 7×Ac) $^{19}$F-NMR(CDCl$_3$,CFCL$_3$): δ −66.79(t, J=11 Hz, 3F, CF$_3$)

Example 18

Synthesis of O-(methyl-5-acetoamide-4,7,8,9-tetra-O-acetyl-3,5-dideoxy-D-glycero-α-D-galacto-2-nonulopyranosylonate)-2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-18,18,18-trifluoro-2-tetracosaneamide-4-octadecene-1,3-diol (referred to as "Compound (18)" hereinafter)

100 mg (0.058 mmol) of the Compound (17) was dissolved in a mixed solvent of 10 ml of pyridine and 2 ml of water to form a solution. Hydrogen sulfide gas was passed through the solution at a room temperature for 48 hours. After the starting substance was confirmed to disappear, hydrogen sulfide was removed from the reaction mixture and water and pyridine were then distilled off under a reduced pressure. The residue was dissolved in 5 ml of anhydrous dichloromethane to form a solution to which 44 mg (0.12 mmol) of tetracosanoic acid and 35 mg (0.18 mmol) of 1-ethyl-3-(3-dimethylaminoprpyl)carbodiimide hydrochloride (referred to as WSC hereinafter) were added under an argon atmosphere. The reaction mixture was stirred at a room temperature for 16 hours. It was then diluted with dichloromethane, washed with water, dried over anhydrous magnesium sulfate and concentrated under a reduced pressure to obtain a residue. It was subjected to silica gel column chromatography (a packing material: silica gel 60(7734), an eluent: methanol/chloroform=1/60→1/40) to obtain 85 mg of Compound (18). Yield: 71.5%.

$[\alpha]_D^{25}$ +9.3° (c 2.0, CHCl$_3$) IRmax(KBr)(cm$^{-1}$): 3390(NH), 2930,2850(Me, methylene), 1740,1230(ester), 1690,1540(amide), 710(phenyl) NMR(CDCl$_3$,TMS): lactose unit; δ 4.61 (d, J=7.5 Hz, 1H, H-1), 4.83(d, J=8 Hz, 1H, H-1'), 5.00(d, 1H, H-4'), 5.01(d, J=10 Hz,8 Hz, 1H, H-2'), 5.25 (dd, J=9 Hz,7.5 Hz, 1H, H-2), 7.3–8.1 (m, 20H, 4×Ph), sialic acid unit; δ 1.66(dd, J=13 Hz, 13 Hz, 1H, H-3a), 1.84(s, 3H, N—COCH$_3$), 2.58(dd, J=13 Hz, 5 Hz, 1H, H-3e), 3.71(s, 3H, OCH$_3$), 4.86(m, 1H, H-4), ceramide unit; δ 5.63(d, J=9 Hz, 1H, NH), 5.67(dt, J=15 Hz, 7 Hz, 1H, H-5), O-acetyl group; δ 1.99(2), 2.01, 2.015, 2.02, 2.10, 2.18(7s, 21H, 7×Ac) $^{19}$F-NMR(CDCl$_3$,CFCL$_3$): δ −66.79(t, J=11 Hz, 3F, CF$_3$)

Example 19

Synthesis of O-(5-acetoamide-3,5-dideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-18,18,18-trifluoro-2-tetracosaneamide-4-octadecene-1,3-diol (referred to as "Compound (19)" hereinafter)

15 mg (0.28 mmol) of sodium methoxide was added under an argon atmosphere to 80 mg (0.039 mmol) of the Compound (18) dissolved in 3.6 ml of methanol. The resulting mixture was stirred at a room temperature for 9.5 hours. It was cooled to 0° C. and then 0.36 ml of water was added. The resulting mixture was stirred at 0° C. for 10 hours and then subjected to Amberlight IR120 (H+) column chromatography (an eluent: methanol). Eluted portions were concentrated to obtain a residue. It was washed with ether to obtain 39.3 mg of Compound (19). Yield: 76.2%.

$[\alpha]_D^{25}$ −0.27° (c 0.50, 1:1 CHCl$_3$—CH$_3$OH) IRmax(KBr)(cm$^{-1}$): 3390(OH,NH), 2920,2850(Me, methylene), 1725(carbonyl), 1635,1560(amide), NMR(2: 1 CD$_3$OD—CDCl$_3$,TMS): lactose unit; δ 4.30(d, J=8 Hz, 1H, H-1), 4.42(d, J=8 Hz, 1H, H-1'), sialic acid unit; δ 2.02(s, 3H, N—COCH$_3$), 2.79 (dd, J=12 Hz, 4 Hz, 1H, H-3e), ceramide unit; δ 0.88(t, J=7 Hz, 3H, CH$_2$CH$_3$), 2.18(t, J=8 Hz, 2H, CH$_2$CO), 4.21(dd, J=10 Hz,4 Hz, 1H, H-1), 5.46(dd, J=15 Hz,8 Hz, 1H, H-4), 5.70(dt, J=15 Hz, 7 Hz, 1H, H-5) $^{19}$F-NMR(2: 1 CD$_3$OD—CDCl$_3$,CFCL$_3$): d −66.79(t, J=11 Hz, 3F, CF$_3$)

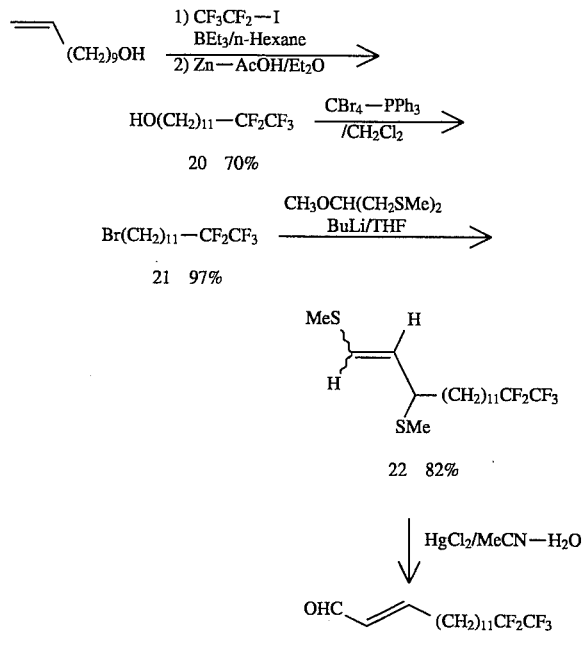

Example 20

Synthesis of 12,12,13,13,13-pentafluorotridecanol (referred to as "Compound (20)" hereinafter)

3.0 ml (15.0 mmol) of 10-undecene-1-ol was dissolved in 110 ml of degassed hexane. 3.5 ml (25.5 mmol) of perfluoroethyl iodide was added 0° C. to the resulting solution. After stirring thereof for 5 minutes, 2.0 ml (2.0 mmol) of 1.0

M triethyl boran in hexane was added thereto to form a mixture which was stirred at 0° C. for 30 minutes and then at room temperature for 30 minutes to form a mixture. A residue which was obtained by condensation of the mixture under a reduced pressure was dissolved in a mixed solvent of 23 ml of ether and 23 ml of acetic acid. 1.35 g (20.7 mmol) of zinc powder was added to the solution at 0° C. and the resulting mixture was stirred at 0° C. for 30 minutes and then at a room temperature for 1 hour and 20 minutes. The reaction mixture was diluted with 200 ml of ether and filtered using Celite. The filtrate was washed with an aqueous 10% potassium hydroxide solution (100 ml×3) and then with an aqueous saturated sodium chloride solution (100 ml), dried over anhydrous magnesium sulfate and concentrated under a reduced pressure to obtain a residue. It was subjected to flash column chromatography (a packing material: silica gel 60K230, an eluent: ethyl acetate/hexane=1/4) to obtain 3.04 g of Compound (20). Yield: 70.0%. Recrystallization thereof from hexane gave a white needle crystal.

m.p. 42.5°–43.5° C. NMR(CDCl$_3$,TMS): δ 3.64(t, J=7 Hz; 2H, CH$_2$—OH), 2.2–1.8(m, 2H, CF$_2$CH$_2$), 1.7–1.2(m, 19H, 9×CH$_2$+OH)

Example 21

Synthesis of 13-bromo-1,1,1,2,2-pentafluorotridecane (referred to as "Compound (21)" hereinafter)

To 1.425 mg (4.91 mmol) of the Compound (21) which had been dissolved in 53 ml of anhydrous dichloromethane, 1.54 g (5.87 mmol) of triphenylphosphine and 2.47 g (7.45 mmol) carbon tetrabromide were added at a room temperature. The mixture was treated with 30 ml of an aqueous saturated sodium bicarbonate solution after 5 minutes. An organic layer was taken and a water layer was extracted with 20 ml of dichloromethane. The organic layers were combined, washed with an aqueous saturated sodium chloride solution, dried over anhydrous magnesium sulfate and concentrated under a reduced pressure to obtain a residue. It was treated with 200 ml of hexane and an undissolved portion was filtered off. The filtrate was concentrated under a reduced pressure to obtain a residue. It was subjected to flash column chromatography (a packing material: silica gel 60K230, an eluent: hexane) to obtain 1.682 g of Compound (21). Yield: 97.0%.

NMR(CDCl$_3$,TMS): δ 3.41(t, J=7 Hz, 2H, CH$_2$—Br), 2.2–1.75(m, 4H, CF$_2$CH$_2$, CH$_2$CH$_2$Br), 1.7–1.2(m, 16H, 8×CH$_2$) $^{19}$F-NMR(CDCl$_3$, CFCL$_3$): δ −85.74(s, 3F, CF$_3$), −118.47(t, J=18 Hz, 2F, CF$_2$)

Example 22

Synthesis of 15,15,16,16,16-pentafluoro-1,3-bis(methylthio)-1-hexadecene (referred to as "Compound (22)" hereinafter)

To 1.36 ml (9.70 mmol) of diisopropylamine and 0.75 g (4.51 mmol) of 1,3-bis(methythio)-2-methoxypropane which had been dissolved in 14 ml of anhydrous terahydrofuran, 5.72 ml (9.15 mmol) of 1.6 M butyl lithium in hexane was added at −78° C. under an argon atmosphere. The mixture was warmed to a room temperature and stirred under an argon atmosphere for 100 minutes. It was again cooled to −78° C. before 1.62 g (4.59 mmol) of the Compound (21) dissolved in 14 ml of anhydrous tetrahydrofuran was dropwise added thereto to form a mixture. It was stirred at −78° C. for 2 hours. 0.4 ml of methanol was added at −78° C., diluted with ether and washed with an aqueous saturated ammonium chloride solution. An organic layer was washed with water and then with an aqueous saturated sodium chloride solution, dried over anhydrous magnesium sulfate and concentrated under a reduced pressure to obtain a residue. It was subjected to flash column chromatography (a packing material: silica gel 60K230, an eluent: dichloromethane/hexane=1/10) to obtain 1.26 g of Compound (22). Yield: 81.7%.

NMR(CDCl$_3$,TMS): δ 6.03(d,J=15 Hz, 1H,C=CHSMe), 5.17(dd, J=15 Hz,9 Hz,1H, CH=CHSMe), 3.12(m, 1H, CH(SMe)—CH=C), 2.27(s, 3H, C=CHSCH$_3$), 1.99(s, 3H, CH—SCH$_3$), 2.2–1.8(m, 2H, CF$_2$CH$_2$), 1.7–1.1(m, 20H, 10×CH$_2$)

Example 23

Synthesis of 15,15,16,16,16-pentafluoro-trans-2-hexadecenal (referred to as "Compound (23)" hereinafter)

To 1.256 mg (3.09 mmol) of the Compound (22) which had been dissolved in a mixed solvent of 8 ml of acetonitrile and 1 ml of water, 3.32 g (12.2 mmol) of mercury chloride (II) was added. The reaction mixture was stirred at 50° C. for 4 hours. After being spontaneously cooled to a room temperature, it was diluted with an aqueous saturated sodium chloride solution. It was extracted with ether. An organic layer was washed with water and then with an aqueous 10% sodium bicarbonate solution, dried over anhydrous magnesium sulfate and concentrated under a reduced pressure to obtain a residue. It was subjected to flash column chromatography (a packing material: silica gel 60K230, an eluent: ether/hexane=1/10) to obtain 0.617 g of Compound (23). Yield: 60.8%.

NMR(CDCl$_3$,TMS): δ 9.51(d, J=8 Hz, 1H, —CHO), 6.86(dt, J=16 Hz,7 Hz, 1H, CH$_2$CH=CH), 6.12(dd, J=16 Hz,8 Hz, 1H, C=CH—CHO), 2.34(dt, J=7 Hz, 7 Hz, 2H, CH$_2$—CH=C), 2.2–1.8(m, 2H, CF$_3$CH$_2$), 1.7–1.2(m, 18H, 9×CH$_2$)

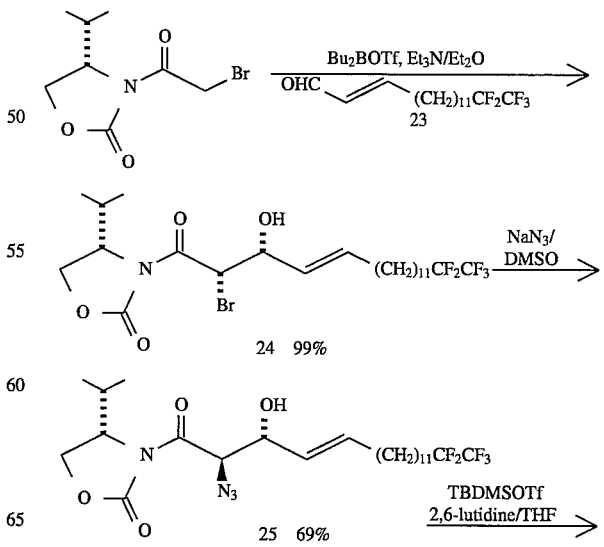

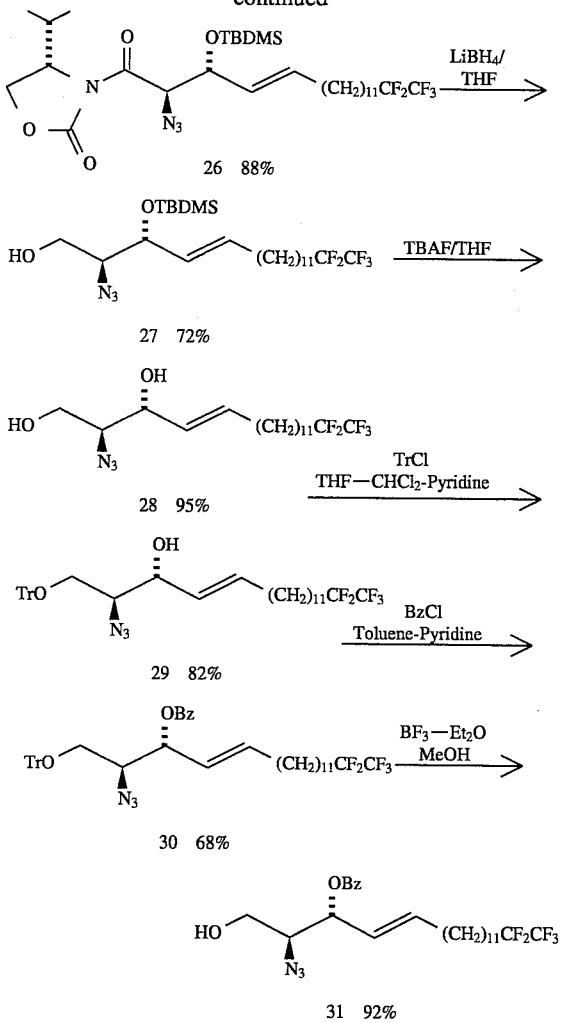

Example 24

Synthesis of
(4S)-3-[(2'S,3'R,4'E)-2'-bromo-17',17',18',18',18'-pentafluoro-3'-hydroxy-4-(isopropyl)-4'-octadecenoyl]-2-oxazolidinone (referred to as "Compound (24)" hereinafter)

To 0.570 g (2.28 mmol) of (4S)-3-(bromoacetyl)-4-(isopropyl)-2-oxazolidinone dissolved in 9 ml of anhydrous ether, 0.45 ml (3.23 mmol) of triethylamine was added at −78° C. under an argon atmosphere to form a solution. After stirring for 5 minutes, 0.58 ml (2.31 mmol) of di-(n-butyl)boron triflate was gradually dropwise added thereto. After the resulting mixture was stirred at −78° C. for 15 minutes, refrigerants were removed and the mixture was stirred at a room temperature for 2 hours. The mixture was again cooled to −78° C. gradually before 0.47 g (1.43 mmol) of the Compound (23) dissolved in 10 ml of anhydrous ether was dropwise added thereto. The resulting mixture was stirred at −78° C. for 45 minutes and then at 0° C. for 1.5 hours before it was diluted with 80 ml of ether. The resulting mixture was poured into 70 ml of an aqueous 1 M sodium hydrogensulfate solution. An organic layer was taken, washed with 30 ml of an aqueous 1 M sodium hydrogensulfate solution and then with an aqueous saturated sodium chloride solution and concentrated under a reduced pressure to obtain a residue. It was again dissolved in 8 ml of ether and cooled to 0° C. A solution of 4 ml of methanol and 4 ml of an aqueous 30% hydrogen peroxide solution was gradually dropwise added and the resulting reaction mixture was stirred at 0° C. for 1 hour. The reaction mixture was diluted with 30 ml of ether and washed with an aqueous saturated sodium bicarbonate solution. A water layer was twice extracted with 20 ml of ether. Organic layers were combined, washed with 30 ml of an aqueous saturated sodium bicarbonate solution and then with 20 ml of an aqueous sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/3) to obtain 0.822 g of Compound (24). Yield: 99.3%.

$[\alpha]_D^{22}$ +42.9° (c 0.225, CHCl$_3$) NMR(CDCl$_3$,TMS): δ 5.85(dt, J=16 Hz, 7 Hz, 1H, CH=CH—CH$_2$), 5.69(d, J=5 Hz, 1H, CHBr), 5.47(dd, J=16 Hz,7 Hz, 1H, CH=CH—CH$_2$), 4.6–4.2(m, 4H, CH$_2$—O, CH—O, CH—NCO), 3.15(bs, 1H, OH), 2.40(m, 1H, CHMe$_2$), 2.2–1.8(m, 4H, CF$_3$CH$_2$, C=C—CH$_2$), 1.7–1.1(m, 18H, 9×CH$_2$), 0.95(d, J=7 Hz, 6H, 2×CH$_3$)

Example 25

Synthesis of
(4S)-3-[(2'R,3'R,4'E)-2'-azide-17',17',18',18',18'-pentafluoro-3'-hydroxy-4-(isopropyl)-4'-octadecenoyl]-2-oxazolidinone (referred to as "Compound (25)" hereinafter)

0.825 g (1.43 mmol) of the Compound (24) was dissolved in 4 ml of dimethyl sulfoxide to form a solution. 0.183 g (2.81 mmol) of sodium azide was added thereto at a room temperature. The resulting mixture was stirred at the room temperature for 2 hours. It was then diluted with 30 ml of ether, washed three times with 10 ml of water and then with 10 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/3) to obtain 0.529 g of Compound (25). Yield: 68.6%.

$[\alpha]_D^{22}$ +18.3° (c 2.25, CHCl$_3$) NMR(CDCl$_3$,TMS): δ 5.90(dt, J=16 Hz, 7 Hz, 1H, CH=CH—CH$_2$), 5.60(dd, J=16 Hz, 7 Hz, 1H, CH=CH—CH$_2$), 5.10(d, J=8 Hz, 1H, CHN$_3$), 4.6–4.2(m, 4H CH$_2$—O, CH—O, CH—NCO), 2.5–2.25(m, 2H, CHMe$_2$, OH), 2.2–1.8(m, 4H, CF$_3$CH$_2$, C=C—CH$_2$), 1.7–1.1(m, 18H, 9×CH$_2$), 0.94 (d, J=7 Hz, 3H, CH$_3$), 0.90 (d, J=8 Hz, 3H, CH$_3$)

Example 26

Synthesis of
(4S)-3-[(2'R,3'R,4'E)-2'-azide-3'-O-tert.-butyldimethylsilyl-17',17',18',18',18'-pentafluoro-3'-hydroxy-4-(isopropyl)-4'-octadecenoyl]-2-oxazolidinone (referred to as "Compound (26)" hereinafter)

0.517 g (0.956 mmol) of the Compound (25) dissolved in 7 ml of anhydrous terahydrofuran was cooled to 0° C. under an argon atmosphere. 0.25 ml (2.15 mmol) of 2,6-lutidine was then added, followed by addition of 0.33 ml (1.44 mmol) of tert.-butyldimethylsilyl triflate to obtain a reaction mixture. The mixture was stirred at 0° C. for 30 minutes. After being stirred at a room temperature for 1 hour, it was diluted with 25 ml of ethyl acetate, washed with 10 ml of water and then with 10 ml of an aqueous sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/6) to obtain 0.554 g of Compound (26). Yield: 88.3%.

$[\alpha]_D^{22}$ −1.63° (c 4.085, CHCl$_3$) NMR(CDCl$_3$,TMS): δ 5.74(dt, J=15 Hz, 6 Hz, 1H, CH=CH—CH$_2$), 5.52(dd, J=15 Hz, 7 Hz, 1H, CH=CH—CH$_2$), 5.21 (d, J=6 Hz, 1H, CHN$_3$), 4.63(dd, J=7 Hz,7 Hz,1H, CHOSi), 4.49(m, 1H, CH—NCO), 4.4–4.2(m, 2H, CH$_2$O),2.3(m, 1H, CHMe$_2$), 2.2–1.8(m, 4H, CF$_2$CH$_2$, C=C—CH$_2$), 1.7–1.1(m, 18H, 9×CH$_2$), 0.95–0.8(m, 15H, 2×CH$_3$, SiCMe$_3$), 0.08(s, 3H, SiCH$_3$), 0.06(s, 3H, SiCH$_3$)

Example 27

Synthesis of (2S,3R,4E)-2-azide-3-O-tert.-butyldimethylsilyl-17,17,18,18,18-pentafluoro-4-octadecene-1,3-diol (referred to as "Compound (27)" hereinafter)

554 mg (0.845 mmol) of the Compound (26) dissolved in 5 ml of anhydrous terahydrofuran was cooled to 0° C. under an argon atmosphere. 55 mg (2.53 mmol) of lithium boron hydride was then added in three portions. The resulting mixture was stirred at 0° C. for 1.5 hours and then at a room temperature for 30 minutes, and again cooled to 0° C. It was diluted with 10 ml of ethyl acetate before 10 ml of an aqueous saturated ammonium chloride solution was gradually added thereto in order to decompose excessive lithium boron hydride. An organic layer was taken and a water layer was extracted with ethyl acetate. The organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/9) to obtain 320 mg of Compound (27). Yield: 71.5%.

$[\alpha]_D^{25}$ −35.6° (c 4.535, CHCl$_3$) NMR(CDCl$_3$,TMS): δ 5.70(dt, J=15 Hz, 7 Hz, 1H, CH=CH—CH$_2$), 5.45(dd, J=15 Hz, 7 Hz, 1H, CH=CH—CH$_2$), 4.22(dd, J=7 Hz,5 Hz, 1H, CHOSi), 3.8–3.6(m, 2H, CH$_2$—OH), 3.41(ddd, 1H, CHN$_3$), 2.2–1.9(m, 5H, CF$_2$CH$_2$, C=C—CH$_2$, OH), 1.7–1.1(m, 18H, 9×CH$_2$), 0.90(s, 9H, SiCMe$_3$), 0.09(s, 3H, SiCH$_3$), 0.05(s, 3H, SiCH$_3$) $^{19}$F-NMR(CDCl$_3$, CFCL$_3$): δ −85.74(s, 3F, CF$_3$), −118.47(t, J=18 Hz, 2F, CF$_2$)

Example 28

Synthesis of (2S,3R,4E)-2-azide-17,17,18,18,18-pentafluoro-4-octadecene-1,3-diol (referred to as "Compound (28)" hereinafter)

302 mg (0.570 mmol) of the Compound (27) dissolved in 6 ml of tetrahydrofuran was cooled to 0° C. under an argon atmosphere. 0.9 ml (0.9 mmol) of 1.0 M tetrabutylammonium fluoride in tetrahydrofuran was then dropwise added. The resulting mixture was stirred at a room temperature for 2 hours. It was diluted with 200 ml of ethyl acetate, washed with water (50 ml×2) and then with 50 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/2) to obtain 226 mg of Compound (28). Yield: 95.4%.

$[\alpha]_D^{25}$ −27.1° (C 4.02, CHCl$_3$) NMR(CDCl$_3$,TMS): δ 5.83(dt, J=16 Hz, 7 Hz, 1H, CH=CH—CH$_2$), 5.54(dd, J=16 Hz, 7 Hz, 1H, CH=CH—CH$_2$), 4.25(m, 1H, CHOH), 3.85–3.65(m, 2H, CH$_2$—OH), 3.51(dt, J=5 Hz, 5 Hz, 1H, CHN$_3$), 2.2–1.9(m, 5H, CF$_3$CH$_2$, C=C—CH$_2$, OH), 1.7–1.1(m, 19H, 9×CH$_2$, OH) $^{19}$F-NMR(CDCl$_3$,CFCL$_3$): δ −85.7(s, 3F, CF$_3$), −118.4(t, J=18 Hz, 2F, CF$_2$)

Example 29

Synthesis of (2S,3R,4E)-2-azide-17,17,18,18,18-pentafluoro-1-triphenylmethoxy-4-octadecene-3-ol (referred to as "Compound (29)" hereinafter)

224 mg (0.539 mmol) of the Compound (27) was dissolved in a mixed solvent of anhydrous tetrahydrofuran-chloroform-pyridine (0.7 ml, 0.7 ml, 0.7 ml) under an argon atmosphere to form a solution. 200 mg (0.717 mmol) of triphenylmethyl chloride was added thereto at 0° C. The mixture was stirred at a room temperature for 50 hours and concentrated under a reduced pressure to obtain a residue. It was dissolved in ether and washed with an aqueous saturated sodium bicarbonate solution. A water layer was extracted with 20 ml of ether twice. Organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/7) to obtain 290 mg of Compound (29). Yield: 81.8%.

$[\alpha]_D^{25}$ −0.16° (C 1.49, CHCl$_3$) NMR(CDCl$_3$,TMS): δ 7.6–7.15(m, 15H, 3×Ph), 5.66(dt, J=15 Hz, 7 Hz, 1H, CH=CH—CH$_2$), 5.32(dd, J=15 Hz,7 Hz,1H,CH=CH—CH$_2$),4.20(m, 1H,CHOH), 3.51(dt, J=5 Hz,5 Hz,1H, CHN$_3$), 3.30(d, J=5 Hz, 2H, CH$_2$-OTr), 2.2–1.9(m, 4H, CF$_2$CH$_2$, C=C—CH$_2$), 1.7–1.1(m, 19H, 9×CH$_2$, OH)

Example 30

Synthesis of (2S,3R,4E)-2-azide-3-benzoyloxy-17,17,18,18,18-pentafluoro-1-triphenylmethoxy-4-octadecene (referred to as "Compound (30)" hereinafter)

290 mg (0.441 mmol) of the Compound (29) was dissolved in a mixed solvent of 2 ml of anhydrous toluene and 0.4 ml of pyridine to form a solution. 0.14 ml (1.21 mmol) of benzoyl chloride was added thereto at 0° C. The mixture was stirred at a room temperature for 13 hours, poured into ice-cooled water and extracted with ether. An organic layer was dried over anhydrous magnesium sulfate and concentrated under a reduced pressure to obtain a residue. It was subjected to flash column chromatography (a packing material: silica gel 60K230, an eluent: ethyl acetate/hexane=1/20) to obtain 228 mg of Compound (30). Yield: 67.9%.

$[\alpha]_D^{23}$ −14.9° (c 3.20, CHCl$_3$) NMR(CDCl$_3$,TMS): δ 8.1–7.1(m, 20H, 4×Ph), 5.82(dt, J=15 Hz, 7 Hz, 1H,CH=CH—CH$_2$), 5.63 (dd, J=9 Hz, 5 Hz, 1H, CHOBz), 5.42(dd, J=15 Hz, 7Hz, 1H, CH=CH—CH$_2$), 3.8(dt, J=6 Hz, 5 Hz, 1H, CHN$_3$), 3.29 and 3.20(dd and dd, 2H, CH$_2$—OTr), 2.2–1.9(m, 4H, CF$_2$CH$_2$, C=C—CH$_2$), 1.7–1.1(m, 18H, 9×CH$_2$)

Example 31

Synthesis of (2S,3R,4E)-2-azide-3-benzoyloxy-17,17,18,18,18-pentafluoro-4-octadecene-1-ol (referred to as "Compound (31)" hereinafter)

To 223 mg (0.293 mmol) of the Compound (30) dissolved in a mixed solvent of 1.1 ml of anhydrous toluene and 0.7 ml of anhydrous methanol, 50 ml (0.407 mmol) of boron trifluoride-diethyl ether complex was dropwise added at 0° C. under an argon atmosphere. The resulting mixture was stirred at a room temperature for 11 hours, poured into an aqueous saturated sodium bicarbonate solution which had been cooled with ice and extracted with ether. An organic layer was dried over anhydrous magnesium sulfate and concentrated under a reduced pressure to obtain a residue. It was subjected to flash column chromatography (a packing material: silica gel 60K230, an eluent: ethyl acetate/hexane= 1/5) to obtain 140 mg of Compound (31). Yield: 92.1%.

$[\alpha]_D^{25}$ −38.7° (c 3.16, CHCl$_3$) NMR(CDCl$_3$,TMS): δ 8.1–7.4(m, 5H, Ph), 6.1–5.8(m, 1H, CHαCH—CH$_2$), 5.7–5.5(m, 2H, CHOBz, CH=CH—CH$_2$), 3.8–3.5(2m, 3H, CHN$_3$, CH$_2$—OH), 2.2–1.7(m, 5H, CF$_2$CH$_2$, C=C—CH$_2$, OH), 1.6–1.2(m, 18H, 9×CH$_2$)

Example 32

Synthesis of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azide-3-O-benzoyl-17,17,18,18,18-pentafluoro-4-octadecene-1,3-diol (referred to as "Compound (32)" hereinafter)

188 mg (0.134 mmol) of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyl trichloroacetoimidate and 140 mg (0.269 mmol) of the Compound (31) were dissolved in 4 ml of anhydrous dichloromethane under an argon atmosphere to form a solution. 2.25 g of Molecular Sieve 4A was added thereto. The resulting mixture was stirred at a room temperature for 30 minutes. It was cooled to 0° C. before 34 ml (0.276 mmol) of boron trifluoride-diethyl ether complex was added. The reaction mixture was stirred at 0° C. for 2 hours. It was filtered using Celite and undissolved

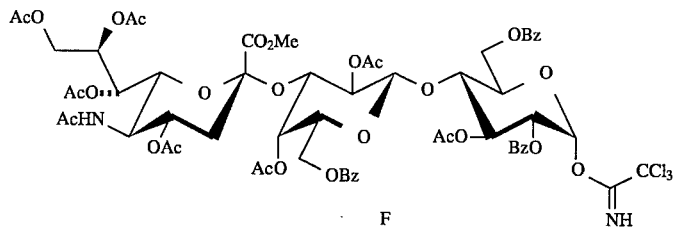

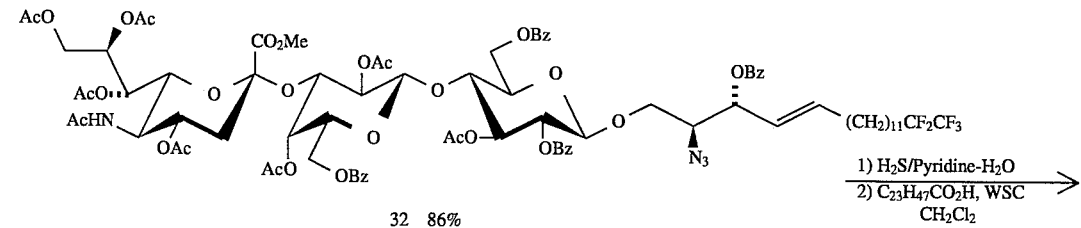

32 86%

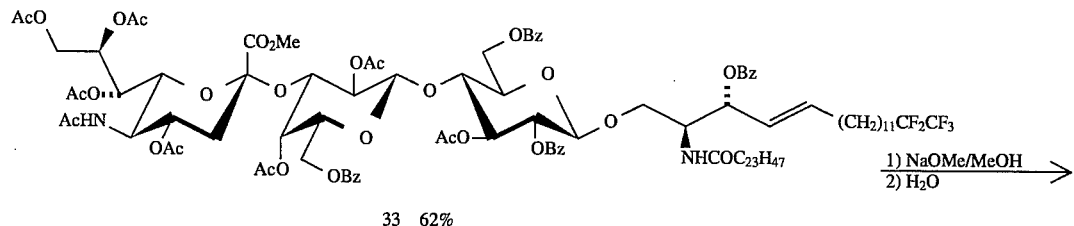

33 62%

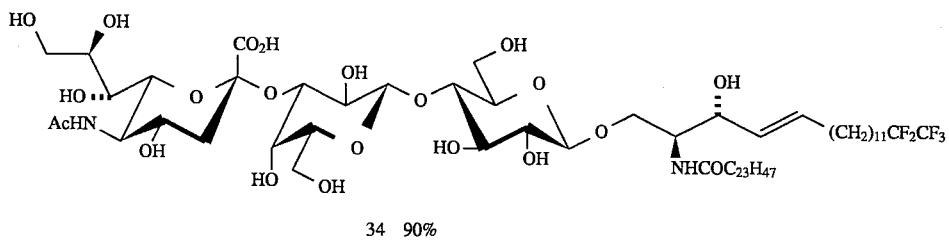

34 90% portion were washed with dichloromethane. The filtrate and the washing liquid were combined, washed with an aqueous 1 M sodium bicarbonate solution and then with water, dried over anhydrous magnesium sulfate and concentrated under a reduced pressure to obtain a residue. It was subjected to flash column chromatography (a packing material: silica gel 60K230, an eluent: ethyl acetate/hexane=3/1) to obtain 204 mg of Compound (32). Yield: 86.4%.

$[\alpha]_D^{25}$ −2.54° (c 0.57, CHCl$_3$) IRmax(KBr)(cm$^{-1}$): 3390(NH), 2105(N3), 1740,1230(ester), 1690,1535(amide), 715(phenyl) NMR(CDCl$_3$,TMS): lactose unit; δ 4.60(dd, J=10 Hz,3 Hz, 1H, H-3'), 4.68(d, J=8 Hz, 1H, H-1), 4.87(d, J=8 Hz, 1H, H-1'), 5.01(d, J=3 Hz, 1H, H-4'), 5.02(dd, 1H, J=10 Hz,8 Hz, H-2'), 5.25(dd, J=9 Hz, 1H, H-2), 7.3–8.1 (m, 20H, 4×Ph), sialic acid unit; δ 1.66(dd, J=13 Hz,13 Hz, 1H, H-3a), 1.84(s, 3H, N—COCH$_3$), 2.57(dd, J=13 Hz, 5 Hz, 1H, H-3e), 3.71(s, 3H, OCH$_3$), 4.85(m, 1H, H-4), ceramide unit; δ 5.67(dt, J=13 Hz, 7 Hz, 1H, H-5), O-acetyl unit; δ 1.98, 1.99, 2.01, 2.02(×2), 2.11, 2.20(7s, 21H, 7×Ac) $^{19}$F-NMR(CDCl$_3$,CFCL$_3$): δ −85.7(s, 3F, CF$_3$), −118.4(t, J=18 Hz, 2F, CF$_2$)

Example 33

Synthesis of
O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3O-acetyl-2,6-di-O-benzoyl-β-D-glucopyranosyl)-(1→1)-(2S,3R,4E)-3-O-benzoyl-17,17,18,18,18-pentafluoro-2-tetracosaneamide-4-octadecene-1,3-diol (referred to as "Compound (33)" hereinafter)

130 mg (0.074 mmol) of the Compound (32) was dissolved in a mixed solvent of 12.5 ml of pyridine and 2.5 ml of water to form a solution. Hydrogen sulfide gas was passed through the solution at a room temperature for 48 hours. After the starting substance was confirmed to disappear, hydrogen sulfide was removed from the reaction mixture, and water and pyridine were then distilled off under a reduced pressure. The residue was dissolved in 6 ml of anhydrous dichloromethane to form a solution to which 35 mg (0.095 mmol) of tetracosanoic acid and 44 mg (0.23 mmol) of WSC were added under an argon atmosphere. The reaction mixture was stirred at a room temperature for 16 hours. It was then diluted with dichloromethane, washed with water, dried over anhydrous magnesium sulfate and concentrated under a reduced pressure to obtain a residue. It was subjected to silica gel column chromatography (a packing material: silica gel 60(7734), an eluent: methanol/chloroform=1/60→1/40)to obtain 96 mg of Compound (33). Yield: 62.4%.

$[\alpha]_D^{25}$ +8.5° (c 2.0, CHCl$_3$) IRmax(KBr)(cm$^{-1}$): 3395(NH), 2930,2855(Me, methylene), 1750,1225(ester), 1685,1530(amide), 715(phenyl) NMR(CDCl$_3$,TMS): lactose unit; δ 4.61(d, J=8 Hz, 1H, H-1), 4.84(d, J=8 Hz, 1H, H-1'), 5.18(dd, J=10 Hz,8 Hz, 1H, H-2), 7.3–8.1 (m, 20H, 4×Ph), sialic acid unit; δ 1.66(dd, J=13 Hz,13 Hz, 1H, H-3a), 1.84(s, 3H, N—COCH$_3$), 2.58(dd, J=13 Hz, 5 Hz, 1H, H-3e), 3.71(s, 3H, OCH$_3$), 4.86(m, 1H, H-4), ceramid unit; δ 5.62(d, J=9 Hz, 1H, NH), 5.76(dt, J=15 Hz, 7 Hz, 1H, H-5), O-acetyl group; δ 1.99(2), 2.01, 2.015, 2.02, 2.10, 2.18(7s, 21H, 7×Ac)

Example 34

Synthesis of
O-(5-acetoamide-3,5-dideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-17,17,18,18,18-pentafluoro-2-tetracosaneamide-4-octadecene-1,3-diol (referred to as "Compound (34)" hereinafter)

17 mg (0.31 mmol) of sodium methoxide was added under an argon atmosphere to 90 mg (0.043 mmol) of the Compound (33) dissolved in 4.0 ml of anhydrous methanol. The resulting mixture was stirred at a room temperature for 15 hours. It was cooled to 0° C. and 0.40 ml of water was then added thereto. The resulting mixture was stirred at 0° C. for 12 hours. It was subjected to Amberlite IR120 column (H+) chromatography (eluent: methanol). Eluted portions were concentrated under a reduced pressure to obtain a residue which was then subjected to column chromatography (packing agent: Sephadex LH-20, an eluent: methanol) to obtain 52.4 mg of Compound (34). Yield: 89.5%.

$[\alpha]_D^{25}$ −0.53° (c 0.50, 1:1 CH$_3$OH—CHCl$_3$) IRmax(KBr)(cm$^{-1}$): 3380(NH), 2920,2850(Me, methylene), 1730(carbonyl), 1640,1555(amide) NMR(2: 1 CD$_3$OD—CDCl$_3$,TMS): lactose unit; δ 4.30(d, J=8 Hz, 1H, H-1), 4.42(d, J=8 Hz, 1H, H-1'), sialic acid unit; δ 2.02(s, 3H, N—COCH$_3$), 2.79(dd, J=12 Hz, 4 Hz, 1H, H-3e), ceramide unit; δ 0.89(t, J=7 Hz, 3H, CH$_2$CH$_3$), 2.18(t, J=8 Hz, 2H, CH$_2$CO), 4.21(dd, J=10 Hz,4 Hz, 1H, H-1), 5.46(dd, J=15 Hz,8 Hz, 1H, H-4), 5.70(dt, J=15 Hz, 7 Hz, 1H, H-5) $^{19}$F-NMR(2: 1 CD$_3$OD—CDCl$_3$): δ −118.0(t, J=18 Hz, 2F, CF$_2$), 85.7(s, 3F, CF$_3$)

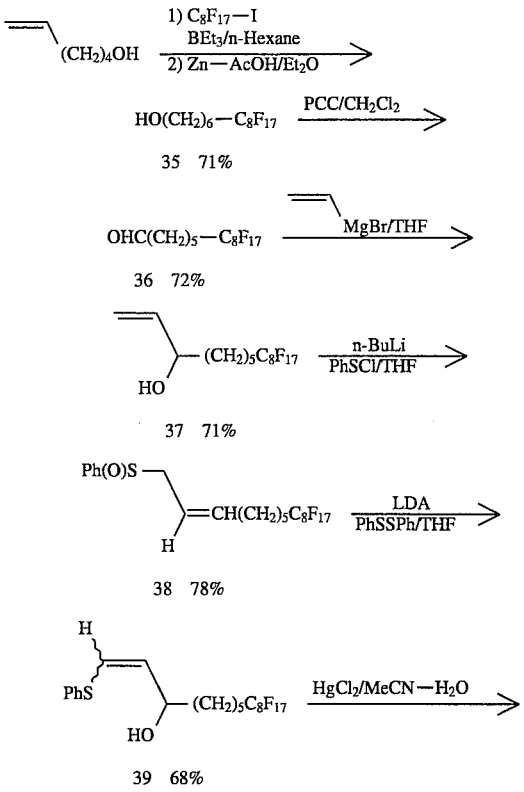

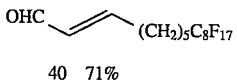

40  71%

Example 35

Synthesis of perfluorooctyl-1-hexanol (referred to as "Compound (35)" hereinafter)

1.0 ml (10.0 mmol) of 5-hexenol was dissolved in 110 ml of degassed hexane to form a solution. 5.46 g (10.0 mmol) of perfluorooctyl iodide was added at 0° C. thereto, followed by the addition of 1.0 ml (1.0 mmol) of 1.0 M triethyl boran in hexane to form a mixture. It was stirred at 0° C. for 30 minutes and then at a room temperature for 30 minutes. A residue which was obtained by concentration of the mixture under a reduced pressure was dissolved in a mixed solvent of 15 ml of ether and 15 ml of acetic acid. 0.90 g (13.8 mmol) of zinc powder was added to the solution at 0° C. and the resulting mixture was stirred at 0° C. for 30 minutes and then at a room temperature for 1 hour and 20 minutes. The reaction mixture was diluted with 200 ml of ether and filtered using Celite. The filtrate was washed with an aqueous 10% sodium hydroxide solution (100 ml×3) and then with an aqueous saturated sodium chloride solution (100 ml), dried over anhydrous magnesium sulfate and concentrated under a reduced pressure to obtain a residue. It was subjected to flash column chromatography (a packing material: silica gel 60K230, an eluent: ethyl acetate/hexane=1/4) to obtain 3.70 mg of Compound (35). Yield: 71.2%. Recrystallization thereof from hexane-ether gave a white needle crystal.

m.p. 56.0°–57.0° C. NMR(CDCl$_3$,TMS): δ 3.66(t, J=6 Hz, 2H, CH$_2$—OH), 2.25–1.85(m, 2H, CF$_2$CH$_2$), 1.7–1.3(m, 9H, 4×CH$_2$+OH)

Example 36

Synthesis of 6-perfluorooctylhexanal (referred to as "Compound (36)" hereinafter)

1.04 g (0.710 mmol) of the Compound (35) dissolved in 15 ml of dichloromethane was added to 770 mg (3.57 mmol) of pyridinium chlorochromate in 6 ml of dichloromethane. The resulting mixture was stirred at a room temperature for 8 hours, then diluted with ether and filtered using Celite. The filtrate was distilled to obtain a residue. It was subjected to flash column chromatography (a packing material: silica gel 60K230, an eluent: ethyl acetate/hexane=1/10) to obtain 750 mg of Compound (36). Yield: 72.4%.

m.p. 31.0°–35.0° C. NMR(CDCl$_3$,TMS): δ 9.79(t, J=1 Hz, 1H, CHO), 2.48(dt, J=7 Hz,1 Hz, 2H,CH$_2$CHO), 2.2–1.85 (m, 2H, CF$_2$CH$_2$), 1.8–1.3(m, 6H, 3×CH$_2$)

Example 37

Synthesis of 8-perfluorooctyl-3-hydroxy-1-octene (referred to as "Compound (37)" hereinafter)

750 mg (1.45 mmol) of the Compound (36) which had been dissolved in 5 ml of anhydrous tetrahydrofuran under an argon atmosphere was dropwise added to 2.6 ml (2.6 mmol) of 1 M vinyl bromide magnesium in tetrahydrofuran under ice-water cooling (about 5° C.). After completion of the dropwise addition, the mixture was warmed to a room temperature, stirred at a room temperature for 30 minutes, and then again cooled with ice-water. The reaction mixture was treated with an aqueous saturated ammonium chloride solution, then extracted with ether. An organic layer was washed with an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/4) to obtain 560 mg of Compound (37). Yield: 70.8%. NMR(CDCl$_3$,TMS): δ 5.88(ddd, J=17 Hz,10 Hz,6 Hz, 1H, —CH═C), 5.18(m, 2H, C═CH$_2$), 4.11(q, J=6 Hz, 1H, CH—(OH)), 2.25–1.85(m, 2H, CF$_2$CH$_2$), 1.8–1.25(m, 9H, 4×CH$_2$+OH) $^{19}$F-NMR(CDCl$_3$,CFCL$_3$): δ –126.3(s,2F, CH$_2$CF$_2$),–121.5–124.0(m,10F, CH$_2$CF$_2$(CF$_2$)$_5$CF$_2$CF$_3$), –114.6(m, 2F, CF$_2$CF$_2$CF$_3$), –81.0(t, J=10 Hz, 3F, CF$_3$).

Example 38

Synthesis of [(2E)-8-perfluorooctyl-2-octenyl]phenyl sulfoxide (referred to as "Compound (38)" hereinafter)

To 5.00 g (9.15 mmol) of the Compound (37) which had been dissolved in 40 ml of anhydrous tetrahydrofuran under an argon atmosphere, 5.8 ml (9.28 mmol) of 1.46 M butyl lithium in hexane was dropwise added at –20° C. to obtain a mixture. 1.56 g (10.8 mmol) of benzenesulfenyl chloride in 2 ml of anhydrous terahydrofuran was added thereto at –20° C. The resulting mixture was heated to a room temperature, stirred for 15 minutes, concentrated under a reduced pressure to obtain a residue. It was diluted with ether, washed with an aqueous saturated sodium chloride solution, dried over anhydrous magnesium sulfate and concentrated under a reduced pressure to obtain a residue. It was subjected to flash column chromatography (a packing material: silica gel 60K230, an eluent: ether/hexane=1/1) to obtain 4.69 g of Compound (38). Yield: 78.3%.

m.p. 44.5°–46.0° C. NMR(CDCl$_3$,TMS): δ 7.7–7.4(m, 5H, aromatic), 5.56(dt, J=15 Hz, 7 Hz, 1H, C═CHCH$_2$S), 5.30(dt, J=15 Hz, 7 Hz, 1H, C—CH$_2$CH═CH—), 3.49(m, 2H, CH$_2$—S(O)Ph), 2.2–1.85(m, 4H, CF$_2$CH$_2$+C—CH$_2$—CH═CH), 1.7–1.2(m, 6H, 3×CH$_2$)

Example 39

Synthesis of (8-perfluorooctyl-3-hydroxy-1-octenyl)phenyl sulfide (referred to as "Compound (39)" hereinafter)

To 1.1 ml (7.85 mmol) of diisobutylamine which had been dissolved in 15 ml of anhydrous tetrahydrofuran at an argon atmosphere, 3.4 ml (6.12 mmol) of 1.46 M butyl lithium in hexane was dropwise added at –78° C. to obtain a mixture. It was stirred at –78° C. for 15 minutes, before 4.0 g (6.11 mmol) of the Compound (38) in 5 ml of anhydrous terahydrofuran was added at a stroke thereto. The resulting mixture was stirred at –78° C. for 1 hour and then at temperatures of –65° to –60° C. for 1 hour and again cooled to –78° C. The reaction mixture above was added through a cannula to 1.39 g (6.37 mmol) of diphenyl disulfide in 10 ml of anhydrous terahydrofuran. After being stirred at 0° C. for 1 hour, the solution was poured into 70 ml of an aqueous 10% hydrochloric acid solution and extracted with chloroform. An organic layer was washed with an aqueous saturated sodium bicarbonate solution, dried over anhydrous magnesium sulfate and concentrated under a reduced pressure to obtain a brown oily residue. It was immediately subjected to flash column chromatography (a packing material: silica gel 60K230, an eluent: ethyl acetate/hexane=1/5) to obtain 2.73 g of Compound (39). Yield: 68.3%. NMR(CDCl$_3$,TMS): δ 7.5–7.1(m, 5H, aromatic), 6.43(d, J=15 Hz, 1H, C=CHPh), 5.83(dd, J=15 Hz, 7 Hz, 1H, —CH=C-SPh), 4.17(q, J=7 Hz, 1H, CH(OH)), 2.25–1.85(m, 2H, CF$_2$CH$_2$), 1.8–1.3(m, 9H, 4×CH$_2$+OH)

Example 40

Synthesis of 8-perfluorooctyl-trans-1-octenal (referred to as "Compound (40)" hereinafter)

To 2.73 g (4.17 mmol) of the Compound (39) which had been dissolved in a mixed solvent of 42 ml of acetonitrile and 9 ml of water, 1.19 g (4.38 mmol) of mercury chloride (11) was added. The reaction mixture was stirred at temperatures of 40° to 50° C. for 15 hours, spontaneously cooled to a room temperature and filtered using Celite. Undissolved portions were washed with chloroform. The filtrate and the washing liquid were combined, washed with an aqueous 10% sodium bicarbonate solution. A water layer was extracted with chloroform. Organic layers were combined, dried over anhydrous magnesium sulfate and concentrated under a reduced pressure to obtain a residue. It was subjected to flash column chromatography (a packing material: silica gel 60K230, an eluent: ether/hexane=1/10) to obtain 1.61 g of Compound (40). Yield: 70.9%. NMR(CDCl$_3$,TMS): δ 9.52(d, J=8 Hz, 1H, —CHO), 6.85(dt, J=16 Hz,7 Hz, 1H, CH$_2$CH=CH) 6.13(dd, J=16 Hz,8 Hz, 1H, C=CH—CHO), 2.38(dt, J=7 Hz, 7 Hz, 2H, CH$_2$—CH=C), 2.25–1.9(m, 2H, CF$_3$CH$_2$), 1.8–1.3(m, 6H, 3×CH$_2$)

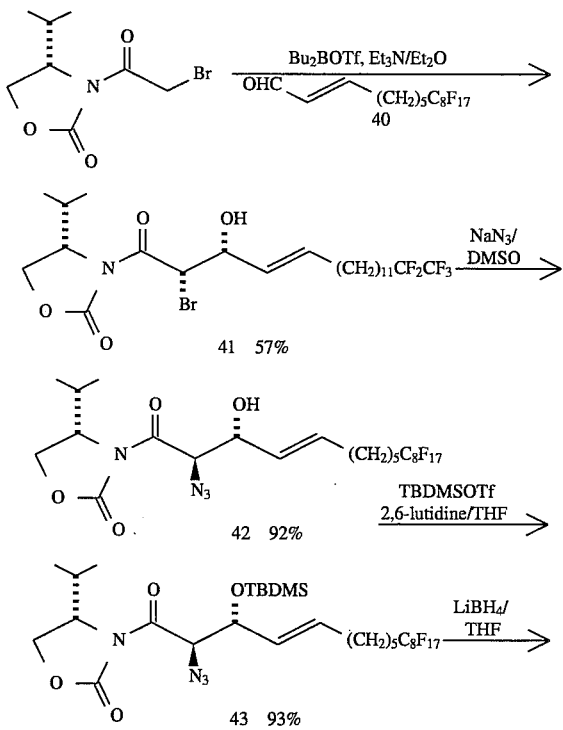

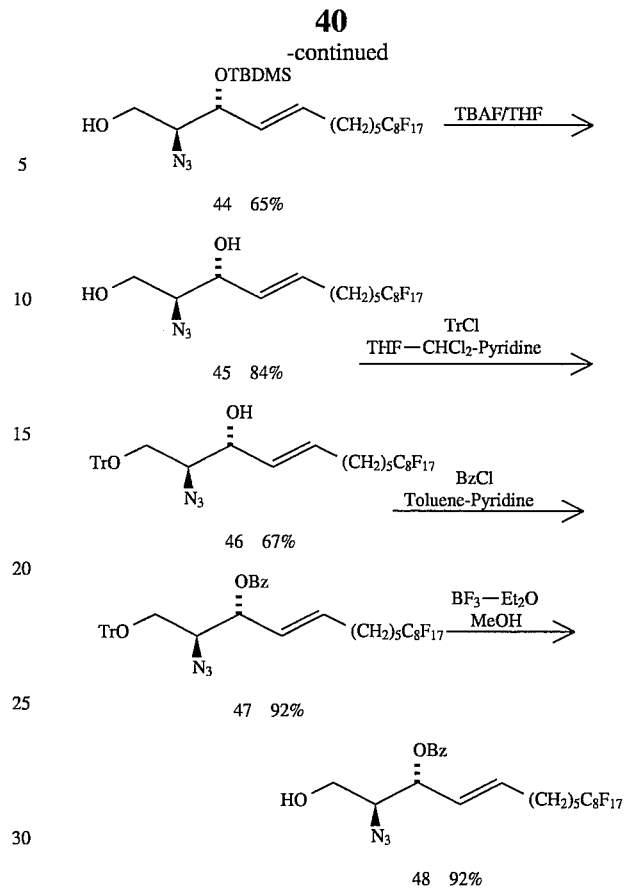

Example 41

Synthesis of (4S)-3-[(2'S,3'R,4'E)-2'-bromo-10-perfluorooctyl-3'-hydroxy-4-(isopropyl)-4'-decenoyl]-2-oxazolidinone (referred to as "Compound (41)" hereinafter)

To 0.55 g (2.20 mmol) of (4S)-3-(bromoacetyl)-4-(isopropyl)-2-oxazolidinone dissolved in 8 ml of anhydrous ether, 0.43 ml (3.09 mmol) of triethylamine was added at −78° C. under an argon atmosphere. After stirring for 5 minutes, 0.56 ml (2.22 mmol) of di-(n-butyl)boron triflate was gradually dropwise added. After the resulting mixture was stirred at −78C. for 15 minutes, refrigerants were removed and the mixture was stirred at a room temperature for 2 hours. The mixture was again cooled to −78° C. gradually before 0.75 g (1.38 mmol) of the Compound (40) dissolved in 8 ml of anhydrous ether was dropwise added thereto. The resulting mixture was stirred at −78° C. for 45 minutes and then at 0° C. for 1.5 hours before it was diluted with 80 ml of ether. The resulting mixture was poured into 70 ml of an aqueous 1 M sodium hydrogensulfate solution. An organic layer was taken, washed with 30 ml of an aqueous 1 M sodium hydrogensufate solution and then with 50 ml of an aqueous saturated sodium chloride solution, and concentrated under a reduced pressure to obtain a residue. It was again dissolved in 10 ml of ether and cooled to 0° C. A mixed solution of 5 ml of methanol and 5 ml of a aqueous 30% hydrogen peroxide solution was gradually dropwise added and the resulting reaction mixture was stirred at 0° C. for 1 hour. The reaction mixture was diluted with 30 ml of ether and washed with an aqueous saturated sodium bicarbonate solution before a water layer was twice extracted with 20 ml of ether. Organic layers were combined, washed with 20 ml of an aqueous saturated sodium bicarbonate solution and then with 20 ml of an aqueous sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane =1/2) to obtain 623 mg of Compound (41). Yield: 56.9%.

m.p. 71°–75° C. $[\alpha]_D^{22}$ +30.1° (c 0.256, CHCl$_3$) NMR(CDCl$_3$,TMS): δ 5.85(dt, J=15 Hz, 7 Hz, 1H, CH=CH—CH$_2$), 5.68(d, J=5 Hz, 1H, CHBr), 5.49(dd, J=15 Hz,6 Hz, 1H, CH=CH—CH$_2$), 4.6–4.2(m, 4H, CH$_2$—O, CH—O, CH—NCO), 3.15(bs, 1H, OH), 2.40(m, 1H, CHMe$_2$), 2.2–1.9(m, 4H, CF$_2$CH$_2$, C=C—CH$_2$), 1.7–1.25(m, 6H, 3×CH$_2$), 0.95(d, J=7 Hz, 6H, 2×CH$_3$)

Example 42

Synthesis of
(4S)-3-[(2'R,3'R,4'E)-2'-azido-10-perfluorooctyl-3'-hydroxy-4-(isopropyl)-4'-decenoyl]-2-oxazolidinone (referred to as "Compound (42)" hereinafter)

0.58 g (0.73 mmol) of the Compound (41) was dissolved in 4 ml of dimethyl sulfoxide to form a solution. 0.10 g (1.54 mmol) of sodium azide was added thereto at a room temperature to obtain a reaction mixture. The mixture was stirred at a room temperature for 3 hours. It was then diluted with 30 ml of ether, washed three times with 10 ml of water and then with 10 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/3) to obtain 0.51 g of Compound (42). Yield: 92.3%.

m.p. 64°–66° C. $[\alpha]_D^{22}$ +17.4° (c 2.40, CHCl$_3$) NMR(CDCl$_3$,TMS): δ 5.89(dt,J=16 Hz, 7 Hz, 1H, CH=CH—CH$_2$), 5.62(dd, J=16 Hz, 7 Hz, 1H, CH=CH—CH$_2$), 5.10(d, J=8 Hz, 1H, CHN$_3$), 4.6–4.2(m, 4H, CH$_2$—O, CH—O, CH—NCO), 2.6–2.25(m, 6H, 3×CH$_2$), 0.94(d, J=8 Hz, 3H, CH$_3$), 0.90(d, J=7 Hz, 3H, CH$_3$)

Example 43

Synthesis of
(4S)-3-[(2'R,3'R,4'E)-2'-azido-3'-O-tert.-butyldimethylsilyl-10'-perfluorooctyl-3'-hydroxy-4-(isopropyl)-4'-decenoyl]-2-oxazolidinone (referred to as "Compound (43)" hereinafter)

445 mg (0.588 mmol) of the Compound (42) dissolved in 3 ml of anhydrous terahydrofuran was cooled to 0° C. under an argon atmosphere. 0.14 ml (1.20 mmol) of 2,6-lutidine was then added, followed by addition of 0.20 ml (0.871 mmol) of tert.-butyldimethylsilyl triflate to obtain a reaction mixture. The mixture was stirred at 0° C. for 30 minutes and then at a room temperature for 1 hour. It was then diluted with 25 ml of ethyl acetate, washed with 10 ml of water and then with 10 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/6) to obtain 475 mg of Compound (43). Yield: 92.7%.

m.p. 69.2°–70.2° C. $[\alpha]_D^{22}$ –0.672° (c 4.02, CHCl$_3$) NMR(CDCl$_3$,TMS): δ 5.73(dt, J=16 Hz, 6 Hz, 1H, CH=CH—CH$_2$), 5.54(dd, J=16 Hz, 8 Hz, 1H, CH=CH—CH$_2$), 5.22(d, J=6 Hz, 1H, CHN$_3$), 4.64(dd, J=8 Hz,6 Hz, 1H, CHOSi), 4.48(m, 1H, CH—NCO), 4.4–4.2(m, 2H, CH$_2$—O), 2.3(m, 1H, CHMe$_2$), 2.2–1.85(m, 4H, CF$_2$CH$_2$, C=C—CH$_2$), 1.7–1.3(m, 6H, 3×CH$_2$), 0.95–0.8(m, 15H, 2×CH$_3$, SiCMe$_3$), 0.08(s, 3H, SiCH$_3$), 0.05(s, 3H, SiCH$_3$)

Example 44

Synthesis of
(2S,3R,4E)-2-azide-3-O-(tert.-butyldimethylsily)-10-perfluorooctyl-4-decene-1,3-diol (referred to as "Compound (44)" hereinafter)

475 mg (0.546 mmol) of the Compound (43) dissolved in 4 ml of anhydrous terahydrofuran was cooled to 0° C. under an argon atmosphere. 40 mg (1.84 mmol) of lithium boron hydride was then added in three portions. The resulting mixture was stirred at 0° C. for 1.5 hours and then at a room temperature for 30 minutes, and again cooled to 0° C. It was diluted with 10 ml of ethyl acetate before 10 ml of an aqueous saturated ammonium chloride solution was gradually added in order to decompose excessive lithium boron hydride. An organic layer was taken and a water layer was extracted with ethyl acetate.. The organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/9) to obtain 263 mg of Compound (44). Yield: 64.8%.

$[\alpha]_D^{25}$ –25.57° (c 4.55, CHCl$_3$) NMR(CDCl$_3$,TMS): δ 5.70(dt, J=16 Hz, 7 Hz, 1H, CH=CH—CH$_2$), 5.48(dd, J=16 Hz, 7 Hz, 1H, CH=CH—CH$_2$), 4.22(dd, J=7 Hz,5 Hz, 1H, CHOSi), 3.8–3.6(m, 2H, CH$_2$—OH), 3.41(ddd, 1H, CHN$_3$), 2.2–1.9(m, 5H, CF$_2$CH$_2$, C=C—CH$_2$, OH), 1.75–1.3(m, 6H, 3×CH$_2$), 0.90(s, 9H, SiCMe$_3$), 0.09(s, 3H, SiCH$_3$), 0.04(s, 3H, SiCH$_3$) $^{19}$F-NMR(CDCl$_3$, CFCL$_3$): δ –81.0(t, J=10H, 3F, CF$_3$), –114.6(m, 2F, CF$_2$CF$_3$), –120.5–127.0 (m, 12F, 6×CF$_2$)

Example 45

Synthesis of
(2S,3R,4E)-2-azide-10-perfluorooctyl-4-decene-1,3-diol (referred to as "Compound (45)" hereinafter)

263 mg (0.353 mmol) of the Compound (44) dissolved in 4 ml of anhydrous terahydrofuran was cooled to 0° C. under an argon atmosphere. 0.6 ml (0.6 mmol) of 1.0 M tetrabutylammonium fluoride in tetrahydrofuran was then dropwise added. The resulting mixture was stirred at a room temperature for 1.5 hours. It was diluted with 200 ml of ethyl acetate, washed with water (50 ml×2) and then with 50 ml of an aqueous saturated sodium chloride solution, dried over anhydrous magnesium sulfate and concentrated under a reduced pressure to obtain a residue. It was subjected to flash column chromatography (a packing material: silica gel 60K230, an eluent: ethyl acetate/hexane=1/2) to obtain 186 mg of Compound (45). Yield: 83.5%.

m.p. 63°–65° C. $[\alpha]_D^{25}$ –16.9° (C 4.01, CHCl$_3$) NMR(CDCl$_3$,TMS): δ 5.83(dt, J=15 Hz,7Hz, 1H, CH=CH—CH$_2$), 5.55(dd, J=15 Hz,7Hz, 1H, CH=CH—CH$_2$), 4.25(m, 1H, CHOH), 3.85–3.65(m, 2H, CH$_2$—OH), 3.51(dt, J=5 Hz, 5Hz, 1H, CHN$_3$), 2.2–1.85(m, 5H, CF$_2$CH$_2$, C=C—CH$_2$, OH), 1.7–1.2(m, 7H, 3×CH$_2$, OH)

Example 46

Synthesis of (2S,3R,4E)-2-azide-10-perfluorooctyl-1-triphenyl-methoxy-4-decene-3-ol (referred to as "Compound (46)" hereinafter)

180 mg (0.285 mmol) of the Compound (45) was dissolved in a mixed solvent of anhydrous terahydrofuran-chloroform-pyridine (0.4 ml, 0.4 ml, 0.4 ml) under an argon atmosphere to form a solution. 130 mg (0.466 mmol) of triphenylmethyl chloride was added thereto at 0° C. The resulting mixture was stirred at a room temperature for 50 hours and concentrated under a reduced pressure to obtain a residue. It was dissolved in ether and washed with an aqueous saturated sodium bicarbonate solution. A water layer was extracted twice with 20 ml of ether. Organic layers were combined, dried over anhydrous magnesium sulfate and concentrated under a reduced pressure to obtain a residue. It was subjected to flash column chromatography (a packing material: silica gel 60K230, an eluent: ethyl acetate/hexane=1/7) to obtain 167 mg of Compound (46). Yield: 67.0%.

$[\alpha]_D^{25}$ +0.33° (c 2.14, CHCl$_3$) NMR(CDCl$_3$,TMS): δ 7.5–7.15(m, 15H, 3×Ph), 5.66(dt, J=16 Hz, 7 Hz, 1H, CH=CH—CH$_2$), 5.32(dd, J=15 Hz, 7 Hz, 1H, CH=CH—CH$_2$), 4.21 (m, 1H, CHOH), 3.53(dt, J=5 Hz, 5 Hz, 1H, CHN$_3$), 3.30(d, J=5 Hz, 2H, CH$_2$—OTr), 2.2–1.85(m, 4H, CF$_2$CH$_2$, C=C—CH$_2$), 1.7–1.2(m, 7H, 3×CH$_2$, OH)

Example 47

Synthesis of (2S,3R,4E)-2-azide-3-benzoyloxy-10-perfluorooctyl-1-triphenylmethoxy-4-decene (referred to as "Compound (47)" hereinafter)

167 mg (0.191 mmol) of the Compound (46) was dissolved in a mixed solvent of 2 ml of anhydrous toluene and 0.2 ml of pyridine to form a solution. 60 ml (0.52 mmol) of benzoyl chloride was dropwise added thereto at 0° C. The resulting mixture was heated to a room temperature, stirred for 14 hours, poured into ice-cooled water and extracted with ether. An organic layer was dried over anhydrous magnesium sulfate and concentrated under a reduced pressure to obtain a residue. It was subjected to flash column chromatography (a packing material: silica gel 60K230, an eluent: ethyl acetate/hexane=1/17) to obtain 171 mg of Compound (47). Yield: 91.5%

$[\alpha]_D^{23}$ −10.33° (c 3.03, CHCl$_3$) NMR(CDCl$_3$,TMS): δ 8.1–7.1(m, 20H, 4×Ph), 5.81(dt, J=15 Hz, 7 Hz, 1H, CH=CH—CH$_2$), 5.64 (dd, J=8 Hz, 5 Hz, 1H, CHOBz), 5.44(dd, J=15 Hz, 8 Hz, 1H, CH=CH—CH$_2$), 3.83(dt, J=6 Hz, 5 Hz, 1H, CHN$_3$), 3.29 and 3.20(dd and dd, 2H, CH$_2$—OTr), 2.2–1.9(m, 4H, CF$_2$CH$_2$, C=C—CH$_2$), 1.7–1.1(m, 6H, 3×CH$_2$)

Example 48

Synthesis of (2S,3R,4E)-2-azide-3-benzoyloxy-10-perfluorooctyl-4-decene-1-ol (referred to as "Compound (48)" hereinafter)

To 170 mg (0.174 mmol) of the Compound (47) which had been dissolved in a mixed solvent of 1.0 ml of anhydrous toluene and 0.5 ml of anhydrous methanol, 30 ml (0.244 mmol) of boron trifluoridediethyl ether complex was dropwise added at 0° C. under an argon atmosphere. The mixture was stirred at a room temperature for 11 hours, poured into an aqueous saturated sodium bicarbonate solution which had been cooled with ice and extracted with ethyl acetate. An organic layer was dried over anhydrous magnesium sulfate and concentrated under a reduced pressure to obtain a residue. It was subjected to flash column chromatography (a packing material: silica gel 60K230, an eluent: ethyl acetate/hexane=1/3) to obtain 117 mg of Compound (48). Yield: 91.5%.

$[\alpha]_D^{25}$ −25.7° (c 2.36, CHCl$_3$) NMR(CDCl$_3$,TMS): δ 8.1–7.4(m, 5H, Ph), 6.1–5.8(m, 1H, CH=CH—CH$_2$), 5.7–5.5(m, 2H, CHOBz, CH=CH—CH$_2$), 3.9–3.5(2m, 3H, CHN$_3$, CH$_2$—OH), 2.2–1.7(m, 4H, CF$_2$CH$_2$, C=C—CH$_2$), 1.7–1.2(m, 7H, 3×CH$_2$, OH) $^{19}$F-NMR(CDCl$_3$, CFCL$_3$): δ −81.3(t, J=10H, 3F, CF$_3$), −114.8(m, 2F, CF$_2$CF$_3$), −122–124 (m, 10F, 5×CF$_2$), −126.6(s, 2F, CH$_2$CF$_2$)

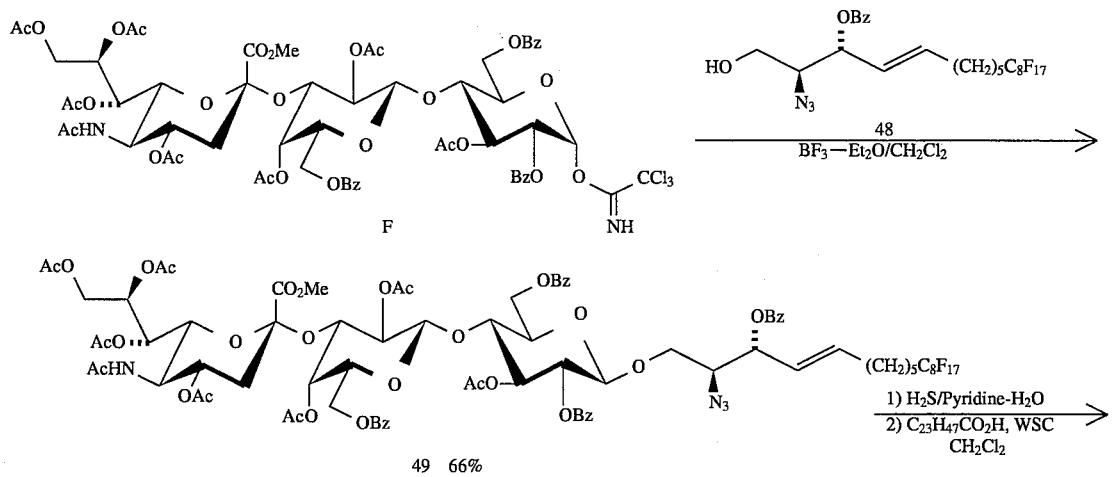

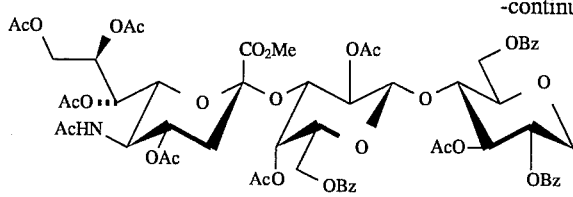
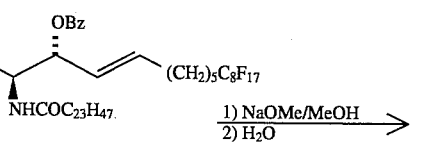
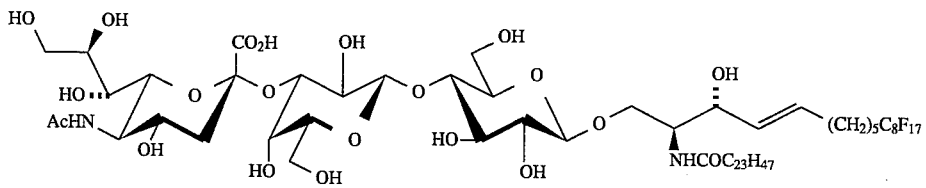

50 74%

51 95%

Example 49

Synthesis of
O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azide-3-O-benzoyl-10-perfluorooctyl-4-decene-1,3-diol (referred to as "Compound (49)" hereinafter)

154 mg (0.110 mmol) of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyl trichloroacetoimidate and 116 mg (0.158 mmol) of the Compound (48) were dissolved in 3 ml of anhydrous dichloromethane under an argon atmosphere to form a solution. 1.9 g of Molecular Sieve 4A was added thereto. The resulting mixture was stirred at a room temperature for 30 minutes. It was cooled to 0° C. before 19 ml (0.154 mmol) of boron trifluoride-diethyl ether complex was added thereto. The resulting mixture was stirred at 0° C. for 4 hours. It was filtered using Celite, and undissolved portions were washed with dichloromethane. The filtrate and the washing liquid were combined, washed with an aqueous 1 M sodium bicarbonate solution and then with water, dried over anhydrous magnesium sulfate and concentrated under a reduced pressure to obtain a residue. It was subjected to flash column chromatography (a packing material: silica gel 60K230, an eluent: ethyl acetate/hexane= 3/1) to obtain 144 mg of Compound (49). Yield: 66,4%.

$[\alpha]_D^{25}$ −1.80° (c 0.58, CHCl$_3$) IRmax(KBr)(cm$^{-1}$): 3390(NH), 2110(N$_3$), 1750,1230(ester), 1690,1540(amide), 715(phenyl) NMR(CDCl$_3$,TMS): lactose unit; δ 4.60(dd, J=10 Hz,3 Hz, 1H, H-3'), 4.68(d, J=8 Hz, 1H, H-1), 4.87(d, J=8 Hz, 1H, H-1'), 5.00(d, J=3 Hz, 1H, H-4'), 5.03(dd, J=10 Hz,8Hz, 1H, H-2'), 5.24(dd, J=10 Hz, J=8 Hz, 1H, H-2), 7.3–8.1 (m, 20H, 4×Ph), sialic acid unit; δ 1.66(dd, J=13 Hz, 13 Hz, 1H, H-3a), 1.84(s, 3H, N—COCH$_3$), 2.57(dd, J=13 Hz, 5 Hz, 1H, H-3e), 3.71(s, 3H, OCH$_3$), 4.85(m, 1H, H-4), ceramide unit; δ 5.67(dt, J=15 Hz, 7 Hz, 1H, H-5), O-acetyl group; δ 1.98, 1.99, 2.01, 2.02(×2), 2.11, 2.20(7s, 21H, 7×Ac) $^{19}$F-NMR(CDCl$_3$, CFCL$_3$): δ −81.0(t, J=10H, 3F, CF$_3$), −114.6(m, 2F, CF$_2$CF$_3$), −121.5–124.0(m, 10F, 5×CF$_2$), −126.3(s, 2F, CH$_2$CF$_2$)

Example 50

Synthesis of
O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-10-perfluorooctyl-2-teracosaneamide-4-decene-1,3-diol (referred to as "Compound (50)" hereinafter)

140 mg (0.071 mmol) of the Compound (49) was dissolved in a mixed solvent of 12 ml of pyridine and 2.4 ml of water to form a solution. Hydrogen sulfide gas was passed through the solution at a room temperature for 50.5 hours. After the starting substance was confirmed to disappear, hydrogen sulfide was removed from the reaction mixture, and water and pyridine was then distilled off under a reduced pressure. The residue was dissolved in 6 ml of anhydrous dichloromethane to form a solution to which 52 mg (0.14 mmol) of tetracosanoic acid and 42 mg (0.22 mmol) of WSC were added under an argon atmosphere. The resulting mixture was stirred at a room temperature for 16 hours. It was then diluted with dichloromethane, washed with water, dried over anhydrous magnesium sulfate and concentrated under a reduced pressure to obtain a residue. It was subjected to silica gel column chromatography (a packing material: silica gel 60(7734), an eluent: methanol/chloroform=1/60→1/40) to obtain 121 mg of Compound (50). Yield: 74.2%.

$[\alpha]_D^{25}$ +8.65° (c 1.85, CHCl$_3$) IRmax(KBr)(cm$^{-1}$): 3390(NH), 2925,2855(Me, methylene), 1750,1230(ester), 1690,1535(amide), 715(phenyl) NMR(CDCl$_3$,TMS): lactose unit; δ 4.60(d, J=8 Hz, 1H, H-1), 4.83(d, J=8 Hz, 1H, H-1'), 5.18(dd, J=10 Hz, 8 Hz, 1H, H-2), 7.3–8.1 (m, 20H, 4×Ph), sialic acid unit; δ 1.66(dd, J=13 Hz, 13 Hz, 1H, H-3a), 1.84(s, 3H, N—COCH$_3$), 2.58(dd, J=13 Hz, 5 Hz, 1H, H-3e), 3.71(s, 3H, OCH$_3$), 4.86(m, 1H, H-4), ceramide unit; δ 5.62(d, J=9 Hz, 1H, NH), 5.76(dt, J=15 Hz, 7 Hz, 1H, H-5), O-acetyl group; δ 1.99, 2.00, 2.02(×2), 2.03, 2.11, 2.18(7s, 21H, 7×Ac)

Example 51

Synthesis of
O-(5-acetoamide-3,5-dideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-10-perfluorooctyl-2-tetracosaneamide-4-decene-1,3-diol (referred to as "Compound (51)" hereinafter)

26 mg (0.48 mmol) of sodium methoxide was added under an argon atmosphere to 119 mg (0.052 mmol) of the Compound (50) dissolved in 4.0 ml of anhydrous methanol. The resulting mixture was stirred at a room temperature for 8 hours. It was cooled to 0° C. and then 0.60 ml of water was added. The resulting mixture was stirred at 0° C. for 4.5 hours. It was subjected to Amberlite IR120 (H+) column chromatography (eluent: methanol). Eluted portions were concentrated under a reduced pressure to obtain a residue which was then subjected to column chromatography (packing agent: Sephadex LH-20, an eluent: methanol) to obtain 77 mg of Compound (51). Yield: 94.6%

$[\alpha]_D^{25}$ +1.72° (c 0.51, 1:1 CH$_3$OH—CHCl$_3$) IRmax(KBr)(cm$^{-1}$): 3380(NH), 2925,2855(Me, methylene), 1730(carbonyl), 1630,1555(amide). NMR(2:1 CD$_3$OD—CDCl$_3$,TMS): lactose unit; δ 4.30(d, J=8 Hz, 1H, H-1), 4.42(d, J=8 Hz, 1H, H-1'), sialic acid unit; δ 2.03(s, 3H, N—COCH$_3$), 2.86(dd, J=12 Hz, 4 Hz, 1H, H-3e), ceramide unit; δ 0.89(t, J=7 Hz, 3H, CH$_2$CH$_3$), 2.18(t, J=8 Hz, 2H, CH$_2$CO), 4.20(dd, J=10 Hz,4 Hz, 1H, H-1), 5.48(dd, J=15 Hz,7 Hz, 1H, H-4), 5.70(dt, J=15 Hz, 7 Hz, 1H, H-5) $^{19}$F-NMR(2:1 CD$_3$OD-CDCl$_3$): δ −81.8(t, J=10H, 3F, CF$_3$), −114.0(m, 2F, CF$_2$CF$_3$), −121–123.5 (m, 10F, 5×CF$_2$), −125.8(s, 2F, CH$_2$CF$_2$)

Example 52

Synthesis of
O-(methyl-5-acetoamide-4,7,8,9-tetra-O-acetyl-3,5-dideoxy-D-glycero-α-D-galacto-2-nonulopyranosylonate)-(2→3)-)-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-2-perfluorononaneamide-10-perfluorooctyl-4-decene-1,3-diol (referred to as "Compound (52)" hereinafter)

109 mg (0.055 mmol) of the Compound (49) was dissolved in a mixed solvent of 8.5 ml of pyridine and 1.7 ml of water to form a solution. Hydrogen sulfide gas was passed through the solution at a room temperature for 48.5 hours. After the starting substance was confirmed to disappear, hydrogen sulfide was removed from the reaction mixture, and water and pyridine was then distilled off under a reduced pressure. The residue was dissolved in 4.6 ml of anhydrous dichloromethane to form a solution, to which 52 mg (0.11 mmol) of perfluorononanoic acid and 35 mg (0.18 mmol) of WSC were added an argon atmosphere. The resulting mixture was stirred at a room temperature for 24 hours. It was then diluted with dichloromethane, washed with water, dried over anhydrous magnesium sulfate and concentrated under a reduced pressure to obtain a residue. It was subjected to silica gel column chromatography (a packing material: silica get 60 (7734), an eluent: diethyl ether/ethyl acetate=3/2) to obtain 99.5 mg of Compound (52). Yield: 75.3%. $[\alpha]_D^{25}$ +8.11° (c 1.03, 1: 1 CH$_3$OH—CHCl$_3$) IRmax(KBr)(cm$^{-1}$): 3390(NH), 2930(methylene), 1745,1235(ester); 1690,1535( amide ), 715(phenyl) NMR(CDCl$_3$,TMS): lactose unit; δ 4.60(d, J=8 Hz, 1H, H-1), 4.84(d, J=8 Hz, 1H, H-1'),

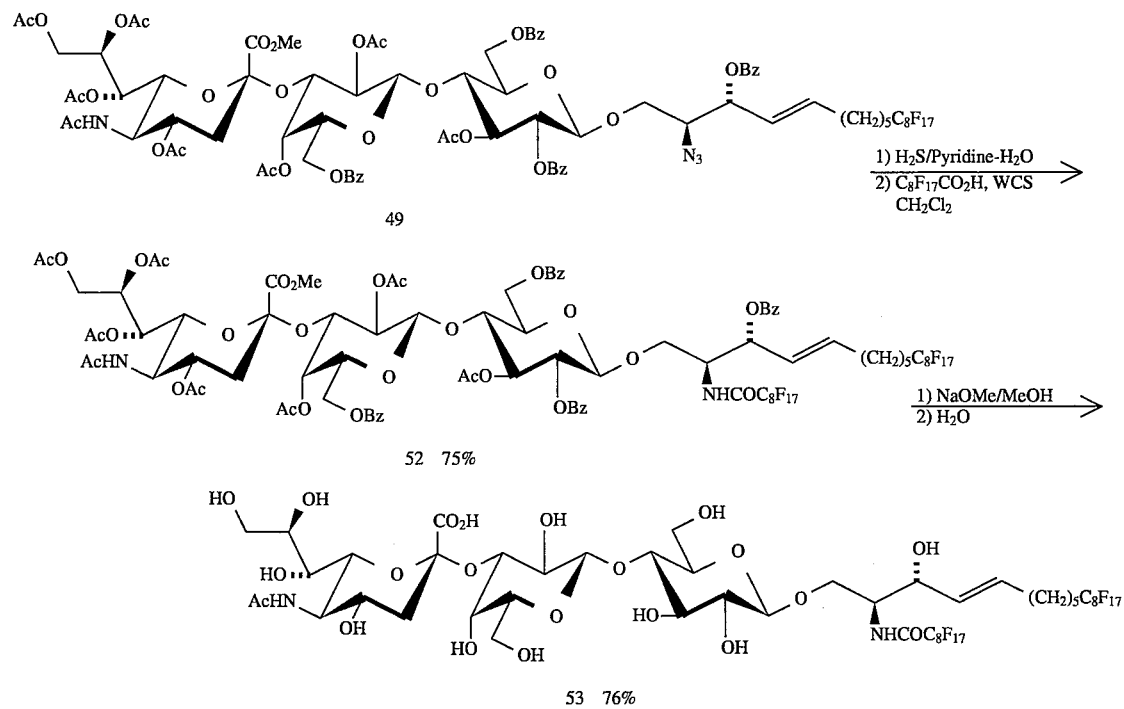

5.17(dd, J=10 Hz, 8 Hz, 1H, H-2), 7.3–8.1 (m, 20H, 4×Ph), sialic acid unit; δ 1.66(dd, J=13 Hz, 13 Hz, 1H, H-3a), 1.84(s, 3H, N—COCH$_3$), 2.57(dd, J=13 Hz, 5 Hz, 1H, H-3e), 3.71(s, 3H, OCH$_3$), 4.86(m, 1H, H-4), ceramide unit;

δ 5.59(d, J=7 Hz, 1H, NH), 5.82(dt, J=15 Hz, 7 Hz, 1H, H-5), O-acetyl group; δ 1.99, 2.00(×2), 2.02(×2), 2.10, 2.18(7s, 21H, 7×Ac)

Example 53

Synthesis of O-(5-acetoamide-3,5-dideoxy-D-glycero-α-D-galacto-2-nonulopyranosylonic acid)-(2→3)-O-(β-D-galactopyranosyl)-(1→4)-O-(β-D-gluocopyranosyl)-(1→1)-(2S,3R,4E)-2-perfluoro-nonaneamid-10-perfluorooctyl-4-decene-1,3-diol (referred to as "Compound (53)" hereinafter)

15 mg (0.28 mmol) of sodium methoxide was added under an argon atmosphere to 95 mg (0.040 mmol) of the Compound (52) dissolved in 3.8 ml of anhydrous methanol. The resulting mixture was stirred at a room temperature for 15 hours. It was cooled to 0° C. and 0.74 ml of water was then added thereto. The resulting mixture was stirred at 0° C. for 3 hours. It was subjected to Amberlite IR120 (H+) column chromatography (eluent: methanol). Eluted portions were concentrated under a reduced pressure to obtain a residue which was then subjected to column chromatography (packing agent: Sephadex LH-20, an eluent: methanol) to obtain 51 mg of Compound (53). Yield: 76.4%

$[\alpha]_D^{25}$ +1.65° (c 0.20, 1: 1 $CH_3OH$—$CHCl_3$) IRmax(KBr)($cm^{-1}$): 3410(NH), 2940(methylene), 1710(carbonyl), 1620,1560(amide) NMR(2: 1 $CD_3OD$-$CDCl_3$,TMS): lactose unit; δ 4.31 (d, J=8 Hz, 1H, H-1), 4.41 (d, J=8 Hz, 1H, H-1'), sialic acid unit; δ 2.03(s, 3H, N—$COCH_3$), 2.83(dd, J=12 Hz, 4 Hz, 1H, H-3e), ceramide unit; δ 4.20(dd, J=8 Hz,4 Hz, 1H, H-1), 5.45(dd, J=15 Hz,8 Hz, 1H, H-4), 5.73(dt, J=15 Hz, 7 Hz, 1H, H-5) $^{19}$F-NMR(2: 1 $CD_3OD$—$CDCl_3$): δ −81.19(t, J=11H, 3F, $CF_3$), −81.17(t, J=11H, 3F, $CF_3$), −114.6(m, 2F, $CF_2CF_3$), −119.6(m, 2F, $CF_2CF_3$), −121−123.7 (m, 20F, 10×$CF_2$), −125.8(s, 4F, $COCF_2$, $CH_2CF_2$)

Example 54

Synthesis of O-(methyl-5-acetoamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-10-perfluorooctyl-2-perfluorooctylhexadecaneamide-4-decene-1,3-diol (referred to as "Compound (54)" hereinafter)

141 mg (0.072 mmol) of the Compound (49) was dissolved in a mixed solvent of 11.9 ml of pyridine and 2.4 ml of water to form a solution. Hydrogen sulfide gas was passed through the solution at a room temperature for 52 hours. After the starting substance was confirmed to disappear, hydrogen sulfide was removed from the reaction mixture, and water and pyridine were then distilled off under a reduced pressure. The residue was dissolved in 6 ml of anhydrous dichloromethane to form a solution, to which 96.5 mg (0.143 mmol) of perfluorooctylhexadecanoic acid and 42 mg (0.22 mmol) of WSC were added under an argon atmosphere. The reaction mixture was stirred at a room temperature for 11.5 hours. It was then diluted with dichloromethane, washed with water, dried over anhydrous magnesium sulfate and concentrated under a reduced pressure to obtain a residue. It was subjected to silica gel column chromatography (a packing material: silica gel 60 (7734), an eluent: methanol/chloroform=1/60→1/40→1/30) to obtain 120 mg of Compound (54). Yield: 64.5%.

$[\alpha]_D^{25}$ +8.10° (c 2.06, $CHCl_3$) IRmax(KBr)($cm^{-1}$): 3390(NH), 2930,2855(Me, methylene), 1745,1240(ester), 1690,1525(amide), 715(phenyl) NMR($CDCl_3$,TMS): lactose unit; δ 4.61(d, J=8 Hz, 1H, H-1), 4.84(d, J=8 Hz, 1H, H-1'), 5.18(dd, J=10 Hz, 8 Hz, 1H, H-2), 7.3–8.1 (m, 20H, 4×Ph), sialic acid unit; δ 1.66(dd, J=13 Hz, 13 Hz, 1H,

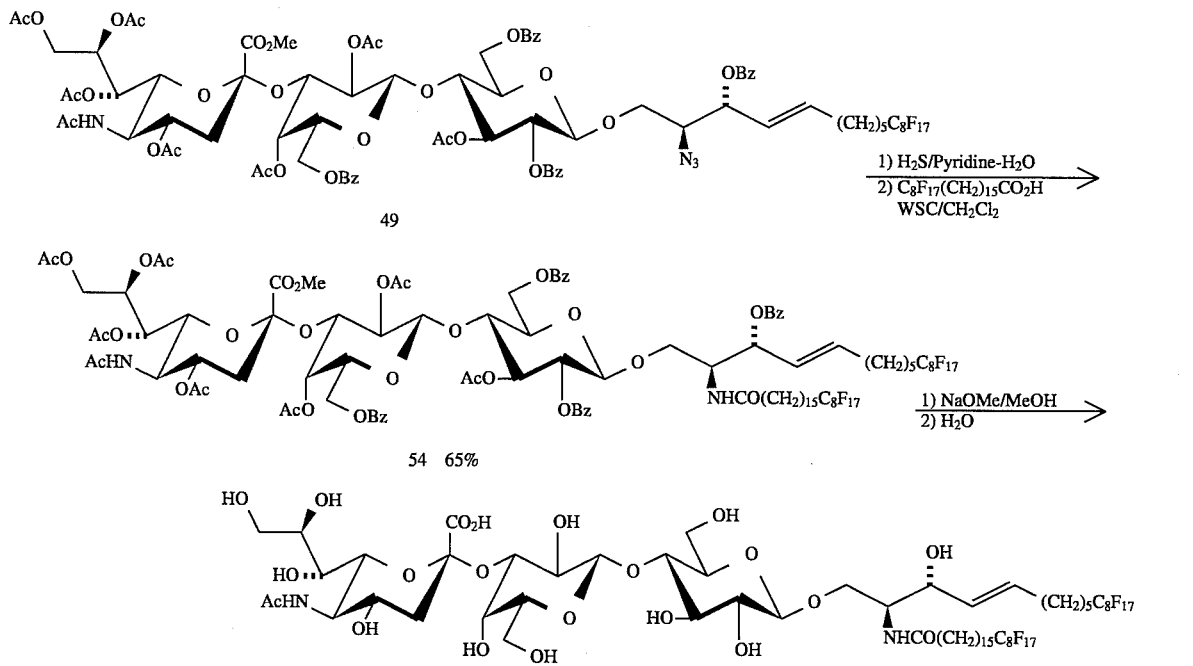

H-3a), 1.84(s, 3H, N—COCH$_3$), 2.57(dd, J=13 Hz, 5 Hz, 1H, H-3e), 3.71(s, 3H, OCH$_3$), 4.87(m, 1H, H-4), ceramide unit; δ 5.65(d, J=9 Hz, 1H, NH), 5.75(dt, J=15 Hz, 7 Hz, 1H, H-5), O-acetyl group; δ7 1.99(×2), 2.01(×2), 2.02, 2.10, 2.18(7s, 21H, 7×Ac)

Example 55

Synthesis of O-(5-acetoamide-3,5-dideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-10-perfluoro-octyl-2-perfluorooctylhexadecaneamide-4-decene-1,3-diol (referred to as "Compound (55)" hereinafter)

17 mg (0.31 mmol) of sodium methoxide was added under an argon atmosphere to 117 mg (0.045 mmol) of the Compound (54) dissolved in 14 ml of anhydrous methanol. The resulting mixture was stirred at a room temperature for 5 hours. It was cooled to 0° C., followed by addition of 0.42 ml of water, and diluted with 8 ml of methanol. The resulting mixture was stirred at a room temperature for 4 hours. It was subjected to Amberlite IR120 column chromatography (eluent: methanol). Eluted portions were concentrated under a reduced pressure to obtain a residue which was then subjected to column chromatography (packing agent: Sephadex LH-20, an eluent: methanol) to obtain 51 mg of Compound (55). Yield: 88.8%

$[α]_D^{24}$ +1.90° (c 0.42, 2: 1 CH$_3$OH—CHCl$_3$) IRmax(KBr)(cm$^{-1}$): 3390(NH), 2930,2855(Me, methylene), 710(carbonyl), 1630,1555(amide) NMR(2: 1 CD$_3$OD—CDCl$_3$, TMS): lactose unit; δ 4.30 (d, J=8 Hz, 1H, H-1), 4.42 (d, J=8 Hz, 1H, H-1'), sialic acid unit; δ 2.03(s, 3H, N—COCH$_3$), 2.85(dd, J=12 Hz, 4 Hz, 1H, H-3e), ceramide unit; δ 4.21(dd, J=10 Hz,4 Hz, 1H, H-1), 5.49(dd, J=15 Hz,8 Hz, H, H-4), 5.70(dt, J=15 Hz, 7 Hz, 1H, H-5). $^{19}$F-NMR(2: 1 CD$_3$OD—CDCl$_3$): δ −81.19(t, J=10H, 6F, 2×CF$_3$), −114.4(m, F, 2×CF$_2$CF$_3$), −121–123.6 (m, 20F, 10×CF$_2$), −126.2(s, 4F, 2×CH$_2$CF$_2$)

The Compound (51) suppresses propagation of cell strain A 31 of normal mouse fibroblast phenotype; thus developing a new area of physiological activity of gangliosides. The fluorinated ganglioside according to the present invention can expected to be useful as a cancerocidal agent, a cancer metastasis suppressing agent, etc., based on a cell propagation suppressing mechanism.

What is claimed is:

1. A compound of the formula:

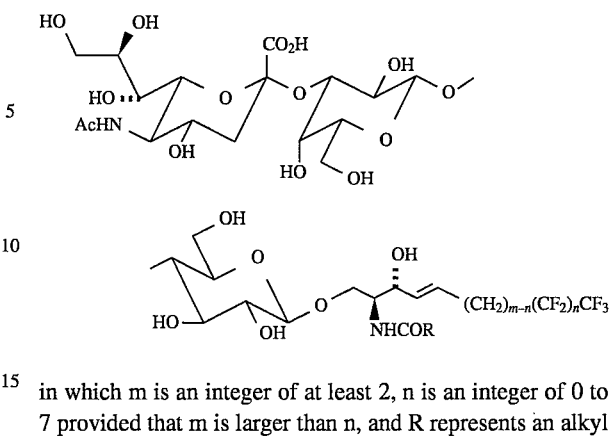

in which m is an integer of at least 2, n is an integer of 0 to 7 provided that m is larger than n, and R represents an alkyl group or a fluoroalkyl group.

2. A compound of the formula

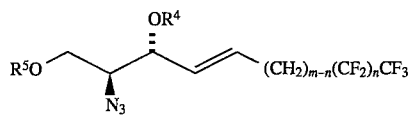

in which m is an integer of at least 2, n is an integer of 0 to 7 provided that m is larger than n, R$^4$ and R$^5$ independently represent a hydrogen atom or a protective group for a hydroxyl group.

3. A compound of the formula:

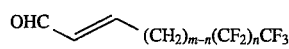

in which m is an integer of at least 2, n is an integer of 0 to 7 provided that m is larger than n.

4. A process for preparing a ganglioside GM3 intermediate of the formula:

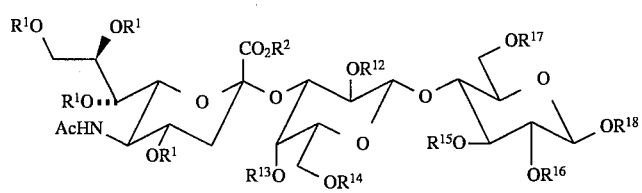

in which R$^1$ represents a protective group for a hydroxyl group, R$^2$ represents a protective group for a carboxylic acid, R$^{12}$, R$^{13}$, R$^{14}$, R$^{15}$, R$^{16}$, and R$^{17}$ independently represent a hydrogen atom or a protective group for a hydroxyl group, and R$^{18}$ represents a trialkylsilylethyl group in which the alkyl group contains 1 to 4 carbon atoms, which comprises the step of reacting a compound of the formula:

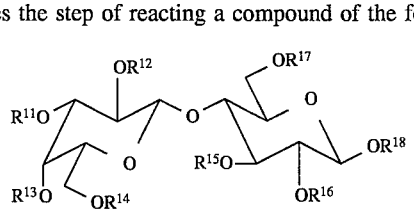

in which R$^{11}$ represents a hydrogen atom or a protective group for a hydroxyl group, and R$^{12}$ to R$^{18}$ are the same as defined above, with a compound of the formula:

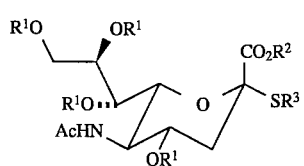
in which $R^1$ and $R^2$ are the same as defined above, and $R^3$ represents an alkyl group containing 1 to 10 carbon atoms or a substituted or unsubstituted phenyl group in the presence of N-iodosuccinimide and trifluoromethanesulfonate.
* * * * *